| United States Patent [19] | [11] | 4,454,314 |
|---|---|---|
| Nagel | [45] | Jun. 12, 1984 |

[54] ANTIBACTERIAL MYCAMINOSYL TYLONOLIDE AND RELATED MACROLIDE DERIVATIVES

[75] Inventor: Arthur A. Nagel, Gales Ferry, Conn.

[73] Assignee: Pfizer Inc., New York, N.Y.

[21] Appl. No.: 404,024

[22] Filed: Aug. 2, 1982

[51] Int. Cl.$^3$ .................. A61K 31/71; C07H 17/08
[52] U.S. Cl. .................................... 536/7.1; 424/180; 424/181
[58] Field of Search .................. 536/7.1; 424/181, 180

[56] References Cited

FOREIGN PATENT DOCUMENTS 56-122397  9/1981  Japan ................................. 536/7.1
2081711  2/1982  United Kingdom ................ 536/7.1

*Primary Examiner*—Johnnie R. Brown

*Attorney, Agent, or Firm*—Charles J. Knuth; Albert E. Frost; Robert K. Blackwood

[57] ABSTRACT

Antibacterial and intermediate substances which are derived by selective chemical transformation of partially hydrolyzed tylosin and related macrolide derivatives in which only the mycaminose sugar remains attached to the macrocyclic lactone ring. Compounds having particular utility as antibacterial agents have C-6 side chain aldehyde converted to a hydrazone, the C-3 ring hydroxy group acylated, and/or the C-14 hydroxymethyl group converted to a sulfonate or carboxylate ester, or to a halomethyl, aminomethyl, sulfonamidomethyl or carboxamidomethyl group. Compounds whose prime utility is as intermediates have side chain aldehyde group protected as an acetal, mycaminose sugar hydroxyls protected as carboxylate ester and/or C-14 hydroxymethyl converted to a formyl or azidomethyl group.

78 Claims, No Drawings

ANTIBACTERIAL MYCAMINOSYL TYLONOLIDE AND RELATED MACROLIDE DERIVATIVES

BACKGROUND OF THE INVENTION

This invention is concerned with antibacterial and intermediate substances which are derived by selective chemical transformation of partially hydrolyzed tylosin and related macrolide derivatives in which only the mycaminose sugar remains attached to the macrocyclic lactone ring. Compounds having particular utility as antibacterial agents have C-6 side chain aldehyde converted to a hydrazone, C-3 ring hydroxy group acylated, and/or C-14 hydroxymethyl group converted to a sulfonate or carboxylate ester, or to a halomethyl, aminomethyl, sulfonamidomethyl or carboxamidomethyl group. Compounds whose prime utility is as intermediates have side chain aldehyde group protected as an acetal, mycaminose sugar hydroxyls protected as a carboxylate ester and/or C-14 hydroxymethyl converted to a formyl or azidomethyl group.

A large number of macrolide antibiotics and derivatives are known to the medicinal sciences, some such as CP-56,063 and CP-56,064 below, only recently discovered.

One of the starting materials for the present invention is tylosin stripped of two of its sugars, so-called desmycarosyl desmycinosyl tylosin, desmycinosyl tylonide or mycaminosyl tylonolide. More systematically, this compound is named 5-(3,6-dideoxy-3-dimethylamino-beta-D-glucopyrnosyloxy)-6-formylmethyl-3-hydroxy-14-hydroxymethyl-4,8,12-trimethyl-9-oxo-10,12-heptadecadien-15-olide. This tylosin degradation product is of the formula (I) below, but has A=OH, Y=oxygen and $R^1$=H. It is reported to be a biosynthetic precursor of tylosin, Omura et al., J. Antibiot. 31, pp. 254-256, 1978. Although originally and vaguely reported as "antibacterial", the prior art has been long silent concerning the specific activity of this compound. Only now has the actual utility and value of this compound as an antibacterial agent been recognized.

Other starting materials, useful in the present invention are derived from CP-56,063 and CP-56,064 via chemical processes and intermediates described below. Similar chemical processes have been previously reported for the selective cleavage of the mycinose sugar from tylosin, Nagel and Vincent, J. Org. Chem. 44, pp. 2050-2052, 1979. The preparation by fermentation and isolation of CP-56,063 and CP-56,064 are also fully disclosed herein.

Umezawa et al., U.S. Pat. Nos. 4,196,280 and 4,255,564 have generally described macrolide derivatives converted to cyclic acetals, then hydrolyzed stepwise, first removing all but mycaminose and finally the mycaminose to yield the acetal of the aglycone. Among the infinity of compounds claimed in U.S. Pat. No. 4,255,564 are compounds of the formula (III) and (IV), but wherein B=$R^6$=H, $A^1$=OH, $R^1$=H or "an acyl group" and $HC(OR^7)_2$ is "an aldehyde group protected by a cyclic acetal". Although claimed, there is no teaching in that patent which would permit preparation of the present compounds of the formula (III) and (IV), wherein B is H, $A^1$ is OH, $R^1$ an acyl group and $HC(OR^7)$ represents an acetal, since the appropriate precursor fermentation macrolides having $R^1$ as acyl required by Umezawa et al. are not known in the present series.

The Umezawa et al. compounds are indicated to be useful for "introducing new sugar moieties or substituents". However the only species disclosed and claimed by Umezawa et al. which is closely related to compounds of the present invention is the compound having the formula (III), but with B=$R^1$=$R^6$=H, $A^1$=OH and both $R^7$ together=—$(CH_2)_2$—. This compound, which appears to be twice claimed (claims 11 and 14 of U.S. Pat. No. 4,255,564) is no more than further degraded by removal of the mycaminose sugar. No method is taught for reintroduction of a sugar or any other group, selectively or otherwise, into either one of these polyhydroxy compounds (mycaminosyl tylonolide acetal and tylonolide acetal).

The corresponding dimethylacetal, of the formula (III) below, but having B=$R^1$=$R^6$=H, $A^1$=OH and $R^7$=$CH_3$ has also been previously reported as an uncharacterized intermediate in the preparation of the corresponding tetrahydro derivative by Omura et al., Tetrahedron Letters No. 12, pp. 1045-1048, 1977. No utility was reported for either this dimethyl acetal or its tetrahydro derivative.

Without a stated utility, Umezawa et al. also appear to claim the aldehydic compound of the formula (I) but wherein A=OH, Y=oxygen and $R^1$=H (claim 13 of U.S. Pat. No. 4,255,564), one of the starting materials employed in the present invention. This product, discussed above and commonly referred to in the literature as mycaminosyl tylonolide, was first reported by Morin and Gorman, Tetrahedron Letters No. 34, pp. 2339-2345 (1964), even before the structure of tylosin was fully established.

Recently Ganguly et al. have reported certain antibacterial hydrazone derivatives of rosaramicin, a macrolide antibiotic having a structure substantially different from the present tylosin/CP-56,063 derivatives.

SUMMARY OF THE INVENTION

The present invention is directed to antibacterial compounds having the formula

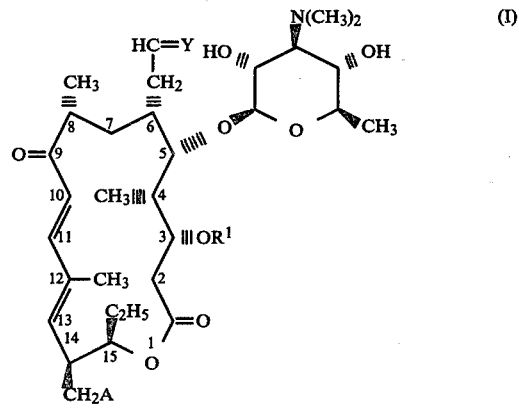

or

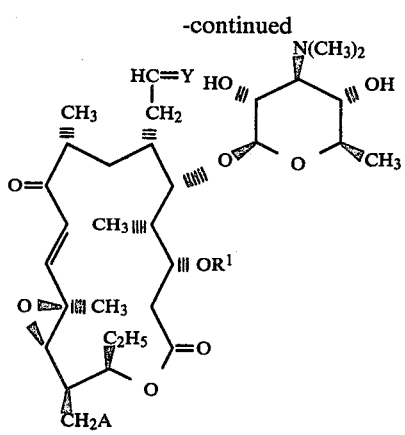

wherein
A is —XR, —OH, —NR²R³ or halo;
X is oxygen or NH;
Y is oxygen or NNR⁴R⁵;
R is $(C_2-C_6)$alkanoyl, $(C_8-C_{10})$phenylalkanoyl, benzoyl, $(C_1-C_6)$alkanesulfonyl or benzenesulfonyl, said phenylalkanoyl, benzoyl and benzenesulfonyl groups optionally mono or disubstituted on aromatic ring with $(C_1-C_3)$alkyl, $(C_1-C_3)$alkoxy or halo;
$R^1$ is hydrogen or $(C_2-C_6)$alkanoyl;
$R^2$ and $R^3$ are each independently $(C_1-C_6)$alkyl, or taken together are —(CH₂)₂O(CH₂)₂— or —(CH₂)ₙ—;
$R^4$ and $R^5$ are each independently H or $(C_1-C_6)$alkyl, or taken together are —(CH₂)₂O(CH₂)₂— or —(CH₂)ₙ—; and
n is an integer from 4 to 7;
with the proviso that when the compound has the formula (I) and A is OH, $R^1$ is other than H;
or a pharmaceutically acceptable acid addition salt thereof. Such salts include, but are not limited to those formed with hydrochloric, hydrobromic, phosphoric, sulfuric, citric, laurylsulfonic, oxalic, maleic, methanesulfonic, p-toluenesulfonic and succinic acid.

At common positions, the present compounds and the fermentation products from which they are ultimately derived have the same absolute stereochemistry, regardless of what that might be. While the absolute stereochemistry is presently believed and understood to be as depicted in the various formulae contained herein, it should be undersood that the intent of these depictions is to show no more than the fact that the derived compounds have the same stereochemistry as the parent fermentation compounds.

Because of their ease of preparation and good antibacterial activity, preferred compounds of the formula (I), wherein A is XR, have (a) X as NH, Y as oxygen, $R^1$ as H and R as benezenesulfonyl, optionally mono or disubstituted, particularly R as p-toluenesulfonyl; (b) X and Y as oxygen, $R^1$ as H and R as acetyl; and (c) X as oxygen, Y as NNR⁴R⁵ and $R^1$ as H, and particularly $R^4$ and $R^5$ as methyl and R as p-toluenesulfonyl. Preferred compounds of the formula (I), wherein A is NR²R³, have Y as oxygen, more preferably $R^2$ and $R^3$ as methyl and $R^1$ as $(C_2-C_6)$alkanoyl, most preferably $R^1$ as acetyl. Preferred compounds of the formula (I) wherein A is OH have $R^1$ as alkanoyl and Y as oxygen, particularly $R^1$ as acetyl. Preferred compounds of the formula (I), wherein A is halo, have (a) $R^1$ as H, Y as oxygen and A as iodo or chloro; and (b) $R^1$ as H, Y as NNR⁴R⁵ and $R^4$ and $R^5$ as methyl, most preferably with A as iodo. Preferred compounds of the formula (II) have A as NR²R³ and Y as oxygen, more preferably with $R^2$ and $R^3$ taken together, particularly as —(CH₂)₇— [also written herein as A=N(CH₂)₇], most preferably with $R^1$ as hydrogen or as acetyl.

The antibacterial activity of the compounds of the formulae (I) and (II) is readily determined by standard methods of serial dilution or disc plate. The latter method in particular is routinely applied to check the susceptibility of microorganisms, including those freshly isolated in clinical practice. The measured antibacterial activity reflects utility in the systemic or topical treatment of animal or human infections due to susceptible bacteria, in animal feeds as growth promotants, in the preservation of substances biogradable by susceptible bacteria or as industrial disinfectants.

The present invention also encompasses compounds primarily useful as intermediates in the synthesis of the present antibacterial compounds. These intermediate compounds are of the formula

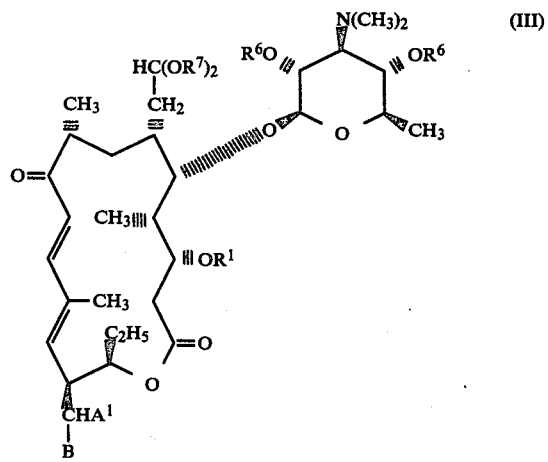

or

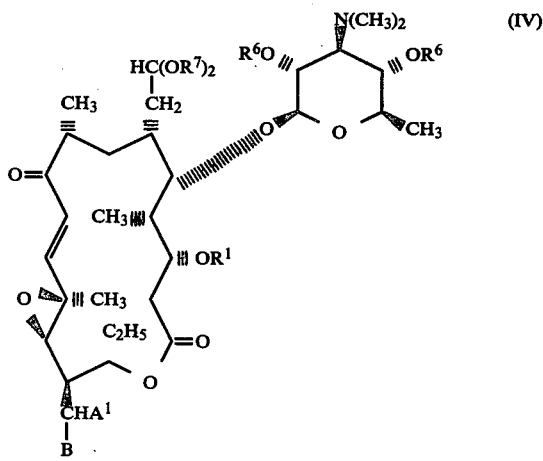

wherein
B is hydrogen and $A^1$ is —XR, —OH, —NH₂, —NR²R³, N₃ or halo; or
B and $A^1$ are taken together and are oxygen;
X is oxygen or NH;

R is $(C_2-C_6)$alkanoyl, $(C_8-C_{10})$phenylalkanoyl, benzoyl, $(C_1-C_6)$alkanesulfonyl or benzenesulfonyl, said phenylalkanoyl, benzoyl and benzenesulfonyl groups optionally mono or disubstituted on aromatic ring with $(C_1-C_3)$alkyl, $(C_1-C_3)$alkoxy or halo;

$R^1$ is hydrogen or $(C_2-C_6)$alkanoyl;

$R^2$ and $R^3$ are each independently $(C_1-C_6)$alkyl, or taken together are $-(CH_2)_2O(CH_2)_2-$ or $-(CH_2)_n-$;

n is an integer from 4 to 7;

$R^6$ is H or $(C_2-C_6)$alkanoyl; and $R^7$ is $(C_1-C_4)$alkyl or the two $R^7$ groups are taken together and are $(C_2-C_3)$alkylene;

with the proviso that when the compound is of the formula (III) and $R^1$ and $R^6$ are both hydrogen, $A^1$ is other than —OH;

or of the formula

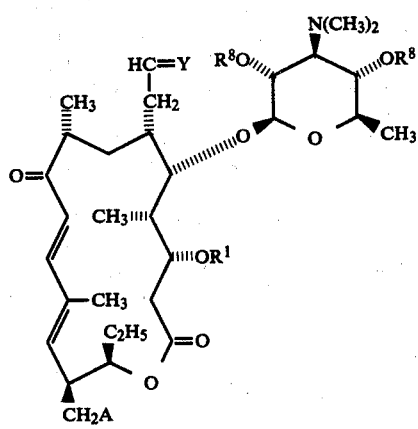

(V)

or

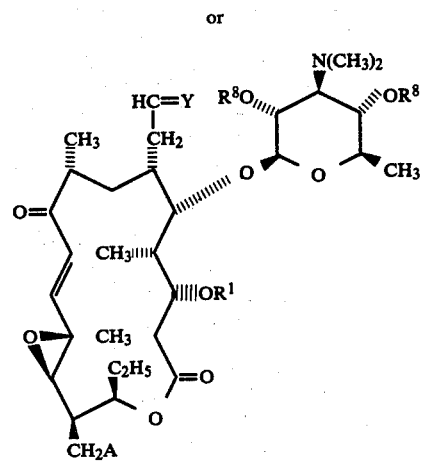

(VI)

wherein

A is —XR, —OH, —$NR^2R^3$ or halo;

X is oxygen or NH;

Y is oxygen or $NNR^4R^5$;

R is $(C_2-C_6)$alkanoyl, $(C_8-C_{10})$phenylalkanoyl, benzoyl, $(C_1-C_6)$alkanesulfonyl or benzenesulfonyl, said phenylalkanoyl, benzoyl and benzenesulfonyl groups optionally mono or disubstituted on aromatic ring with $(C_1-C_3)$alkyl, $(C_1-C_3)$alkoxy or halo;

$R^1$ is hydrogen or $(C_2-C_6)$alkanoyl;

$R^2$ and $R^3$ are each independently $(C_1-C_6)$alkyl, or taken together are $-(CH_2)_2O(CH_2)_2-$ or $-(CH_2)_n-$;

$R^4$ and $R^5$ are each independently H or $(C_1-C_6)$alkyl, or taken together are $-(CH_2)_2O(CH_2)_2-$ or $-(CH_2)_n-$;

n is an integer from 4 to 7; and $R^8$ is $(C_2-C_6)$alkanoyl.

Preferred compounds of the formula (III) to (VI) are those used for the synthesis is preferred compounds of the formula (I) or (II).

DETAILED DESCRIPTION OF THE INVENTION

The antibacterial compounds of the present invention are readily prepared, as appropriate, from (a) mycaminosyl tylonolide, of the formula (I) but wherein A=OH, Y=oxygen and $R^1$=H, a compound alternatively derived from CP-56,064 (formula VII below); or (b) the corresponding compound of the formula (II), wherein A=OH, Y=oxygen and $R^1$=H, derived from CP-56,063 (formula VIII below). When these starting materials are derived from CP-56,064 or CP-56,063, they will generally already have aldehyde and mycaminose hydroxy protecting groups in place. Such protecting groups will frequently not be removed until after further chemical transformations are carried out on the molecule.

The present invention employs a number of unit processes in converting starting compounds to a desired product. It will be evident to one skilled in the art that it is frequently possible to put these processes together in more than one sequence to achieve the desired goal. It will also be evident that introduction of certain protecting groups will necessarily or preferably precede certain of these unit processes, ultimately followed by removal of the protecting group.

Acetal Formation

The acetal in compounds of the formula (III) or (IV) is prepared from the corresponding aldehyde by reaction of at least two molar equivalents of a $(C_1-C_6)$alkanol or one molar equivalent of a $(C_1-C_3$alkylenediol in the presence of a strong acid catalyst, such as HCl or p-toluenesulfonic acid. The alcohol or diol will generally be used in large excess in order to force this equilibrium reaction to completion. The latter can also be achieved by removal of formed water by azeotropic distillation, or by adding a drying agent which will take up water, but not the alcohol. Temperature of the reaction is not critical, e.g., 0°–75° is satisfactory. Conveniently, ambient temperature is used. When a sequence of unit processes also involves acylation of mycaminose hydroxy groups, or formation or reaction of aldehyde at C-14, the present acetal formation will generally be carried out as a prior step.

Specific examples of acetal formation are found under Method G and Preparation 5 below.

Acylation of Mycaminose Hydroxyl Groups

Absent added base, mycaminose hydroxy groups are selectively acylated by the action of at least two molar equivalents of a $(C_2-C_6)$carboxylic acid anhydride, a reaction usually carred out in the presence of a reaction-inert solvent, such as methylene chloride, toluene, ethyl acetate or the like. Temperature is not critical, e.g. 0°–75° C. is satisfactory. Conveniently ambient temperature is used. As used herein, the expression "reaction-inert solvent" is intended to indicate any solvent or diluent which will not interact with reactants, reagents or products in a manner which significantly reduces the yield of the desired product.

When acylation of other hydroxyl groups, or oxidation of hydroxymethyl to formyl is part of the sequence of unit processes, the present acylation will generally be carried out as a prior step.

Specific examples of mycaminose sugar formation are found under Method C and Preparation 6 below.

Acylation of C-14 Hydroxymethyl

With mycaminose hydroxy groups blocked as ($C_2$–$C_6$)alkanoate esters, C-14 hydroxymethyl groups are selectively acylated even in the presence of an unacylated C-3 hydroxyl group, provided that forcing conditions are avoided. This acylation occurs readily at room temperature with at least one equivalent (and usually no more than three equivalents) of the appropriate sulfonyl chloride, or carboxylic acid chloride or anhydride, in the presence of at least one equivalent (and usually no more than three equivalents) of a tertiary amine such as triethylamine or N-methylmorpholine. Optionally, a small but limited portion of the amine is 4-dimethylaminopyridine. Temperature is not critical, but temperatures of 0°–30° C. are preferred when a C-3 hydroxyl group is present. Ambient temperature is usually satisfactory. The reaction is generally carried out in the presence of a reaction-inert solvent, such as methylene chloride, toluene or ethyl acetate.

When the ultimately desired product has both C-3 hydroxy and C-14 hydroxymethyl as ester derivatives, C-14 acylation will generally precede C-3 acylation.

Specific examples of C-14 hydroxymethyl acylation are found below under Method D.

Acylation of C-3 Hydroxy

Except to use more vigorous conditions (e.g. greater excess of acylating agent, greater excess of tertiary amine, particularly including higher levels of 4-dimethylaminopyridine, moderately elevated temperatures, e.g. 30°–75° C., and/or longer reaction times) the acylation of a C-3 hydroxy group is otherwise carried out in a manner analogous to the acylation of the C-14 hydroxymethyl group as detailed above.

If a C-3 acyl, C-14 hydroxymethyl compound is desired (as for oxidation to aldehyde) then the hydroxymethyl group is preliminarily blocked by (1-imidazolyl)carbonylation, accomplished by the action of 1,1-carbonyldiimidazole (substantially one equivalent or slight excess), in a reaction-inert solvent such as methylene chloride, conveniently at ambient temperature. After C-3 acylation, the (1-imidazolyl)carbonyl group is rapidly removed by reaction with $K_2CO_3$ (essentially mole per mole) in an aqueous or aqueous organic solvent, such as 2:1 acetone:water, conveniently at room temperature, where only a short reaction period is required (e.g. 2 hours).

When oxidation of hydroxymethyl to formyl is a step in the sequence of unit processes, the present acylation will generally be carried out as a prior step in order to avoid the complication of oxidation of the C-3 hydroxy group.

Specific examples of C-3 acylation are found under Method L below.

Displacement of Sulfonyloxy with Secondary Amine, Halide or Azide or Displacement with Secondary Amine or Azide These displacement reactions are carried out in a reaction-inert solvent under conditions generally known in the art of organic chemistry. The substrate (sulfonate ester or halide) is contacted in a reaction-inert solvent, usually with an excess of the displacing agent (i.e., the appropriate secondary amine or an alkali metal azide or halide). When the substrate is other than iodide, addition of small amounts of an alkali metal iodide will frequently catalyze the reaction, permitting milder conditions and/or a shorter reaction time to be used. The rate of reaction is generally increased by use of more polar solvent. Lower boiling solvents are preferred, since they are readily recovered from the reaction mixture by stripping in vacuo.

Acetone is particularly well suited for displacement of sulfonate esters with secondary amines, halide or azide (see Methods E, J and O below). Temperature is not critical, but is conveniently at the reflux temperature of acetone in order that the reaction will proceed at a reasonable rate, preferably with iodide present to further enhance the rate. It is understood that, in the presence of iodide, secondary amine and azide displacement occurs via the 14-iodomethyl compound, itself one of the alternative substrates for preparation of the present aminomethyl and azidomethyl secondary derivatives.

When iodide is used as displacing agent, hydrazones tend to concommitantly hydrolyze to aldehyde (cf. Example J1 below).

Selective Replacement of Hydroxymethyl with Halomethyl

Preferably with the mycaminose hydroxy groups protected, a variety of standard methods are available for selective and direct conversion of the C-14 hydroxymethyl to halomethyl. Exemplary is the preparation of the chloromethyl derivative, using triphenylphosphine (at least one and usually 2–3 molar equivalents) in an excess of carbon tetrachloride, conveniently at reflux temperature (See Method H below).

Oxidation of Hydroxymethyl to Formyl

With mycaminose and C-3 hydroxyl as ($C_1$–$C_6$)alkanoates, the C-14 hydroxymethyl group is selectively oxidized to a formyl group. For example, in a reaction-inert solvent such as benzene, the hydroxymethyl compound is reacted with excess dimethylsulfoxide (e.g. 4 molar equivalents) and a lesser excess of a carbodiimide, preferably a water soluble carbodiimide such as 1-(3-dimethylaminopropyl)-3-ethylcarbodiimide (e.g. 3 molar equivalents). After a brief reaction period, pyridinium trifluoroacetate (substantially 1 molar equivalent) is added, resulting in rapid formation of the desired formyl compound. Temperature is not critical, but is preferably about 5°–30° C., conveniently ambient. This unit process is exemplified by Method M below.

Reductive Amination of C-14 Formyl

With C-6 formylmethyl group protected as acetal, a C-14 formyl group is reductively aminated with a secondary amine using a variety of methods standard in the art, e.g., by use of molar equivalent quantities of the amine and aldehyde, hydrogenated over a noble metal catalyst in a reaction-inert solvent. An alternative method, reduction of the aldehyde with sodium cyanoborohydride in a lower alkanol such as methanol, in the presence of excess secondary amine hydrochloride (e.g. 20 molar equivalents), is particularly convenient in the present instance. Excess chemical equivalents of the hydride are generally employed (e.g. 1 mole of NaB(CN)H$_3$ (3 equivalents)/mole of aldehyde). Temperature is not critical, e.g., 0°–50° C. is satisfactory. Conveniently ambient temperature is used. Method N below specifically exemplifies this process.

When the ultimate product desired is a hydrazone, the present reductive amination will generally be carried out prior to such hydrazone formation.

Reduction of Azido to Amino

Reduction of azido to amino is readily accomplished by hydrogenation of any one of a variety of hydrogenating catalysts, including noble metals such as Pd, Rh or Pt (on a carrier such as carbon, as an oxide such as PtO$_2$ or as a salt such as RhCl$_3$), or a moderated noble metal catalyst such as Lindlar's catalyst (palladium moderated with lead acetate and quinoline, Helv. Chim. Acta, 35, p. 446, 1952), the preferred catalyst in the present instance. Temperature is not critical, e.g., 0°–75° C. is satisfactory; conveniently ambient temperature is used. Pressure can be subatmospheric to 100 atmospheres or more, but lower pressures (1 to 7 atmospheres) are preferred. Method D below specifically exemplifies the present reduction, which is preferably carried out on acetal protected compounds, avoiding any possible concomitant reduction of aldehyde or hydrazone.

Selective Acylation of Aminomethyl

Using mild conditions, the present C-14 aminomethyl group is generally selectively acylated, regardless of what other groups are present in the molecule. However, it is preferred to have mycaminose hydroxyls protected as a (C$_2$–C$_6$) alkanoate ester. Conditions are essentially the same as those used to acylate C-14 hydroxymethyl groups but are generally milder (e.g. less excess of acylating agent and tertiary amine, no 4-dimethylaminopyridine, lower temperature and shorter reaction time). Method Q below specifically exemplifies the present N-acylation.

Selective Deacylation of Mycaminose Esters (C$_2$–C$_6$)Alkanoate esters of mycaminose esters are readily and selectively hydrolyzed in methanol. Temperature is not critical, e.g., 0°–50° C. is satisfactory. Conveniently, ambient temperature is employed. Method B below specifically illustrates the present deacylation.

Deacetalization

Deacetalization is readily accomplished by acid catalyzed hydrolysis in an aqueous or aqueous organic solvent such as 1:1 acetonitrile:water or 1:1 ethyl acetate:water. Generally, a relatively strong acid such as difluoroacetic acid or hydrochloric acid, in submolar or multimolar quantities is used as the acid. Temperature is not critical, e.g., 0°–50° C. is satisfactory; conveniently, ambient temperature is used. Method F below provides specific examples of the present deacetalization.

Hydrazone Formation

Hydrazones of the present invention are readily formed by reaction of 6-formylmethyl compounds with the appropriate 1,1-disubstituted hydrazine (substantially one molar equivalent) in a reaction inert solvent, such as a lower secondary alcohol (e.g., 2-propanol). Temperature is not critical, e.g., 0°–50° C. is satisfactory; conveniently ambient temperature is used. When a hydrazone is the ultimately desired product, it is generally carried out at a late stage in the sequence, for example after 14-hydroxymethyl is converted to formyl and reductively aminated.

As noted above, these unit processes are combined in many sequences, to form desired antibacterial products from starting materials in turn derived from tylosin, CP-56,064 or CP-56,063. For example, compound of the formula (IV) wherein B=R$^1$=H, A$^1$=OH, R$^6$=CH$_3$CO and R$^7$=CH$_3$ (derived from CP-56,063 via Preparations 4-11 and Example A1) is converted to (a) compound of the formula (II) wherein A=OH, Y=oxygen and R$^1$=H by deacetalization and mycaminose ester deacylation; (b) compound of the formula (II) wherein A=Br, Y=oxygen and R$^1$=H by conversion of C-14 hydroxymethyl to mesylate ester followed by displacement with bromo and finally deacetalization and acetate hydrolysis; (c) compound of the formula (II) wherein A=OH, Y=NN(CH$_2$)$_6$ and R$^1$=CH$_3$CH$_2$CO by selective C-3 propionylation, deacetalization, hydrazone formation with 1-aminopiperidine, and mycaminose deacetylation; or (d) compound of the formula (II) wherein A=N(CH$_2$CH$_2$)$_2$O, Y=oxygen and R$^1$=OH by selective C-3 acetylation, hydroxymethyl oxidation to formyl, reductive amination using morpholine, deacetalization and mycaminose deacylation. Many other sequences will be evident on review of the specific examples.

The present mycaminosyl tylonolide starting material is derived according to literature methods. Other starting materials are derived from CP-56,064 and CP-56,063, of the formulae

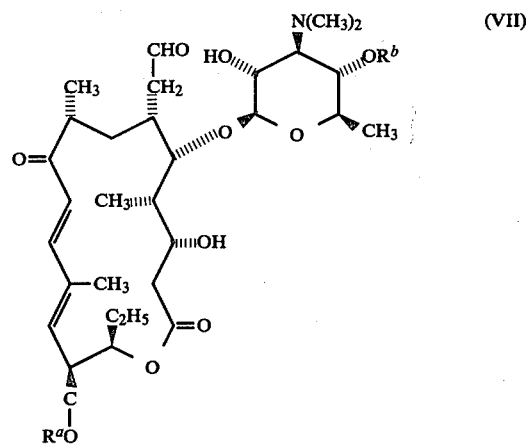

CP-56,064 and

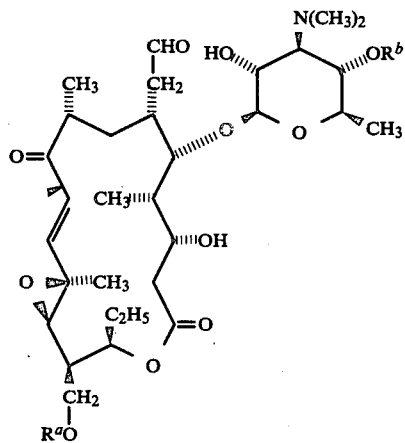

CP-56,063

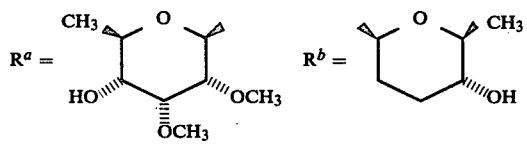

respectively, whose preparation by fermentation and isolation are detailed in Preparations 1–3 below.

CP-56,064 and CP-56,063 are converted to compounds presently useful as starting materials via intermediate compounds of the formulae

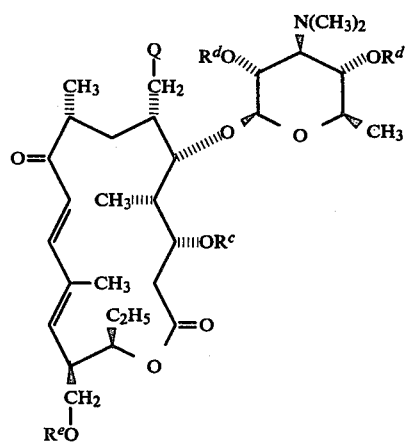

and

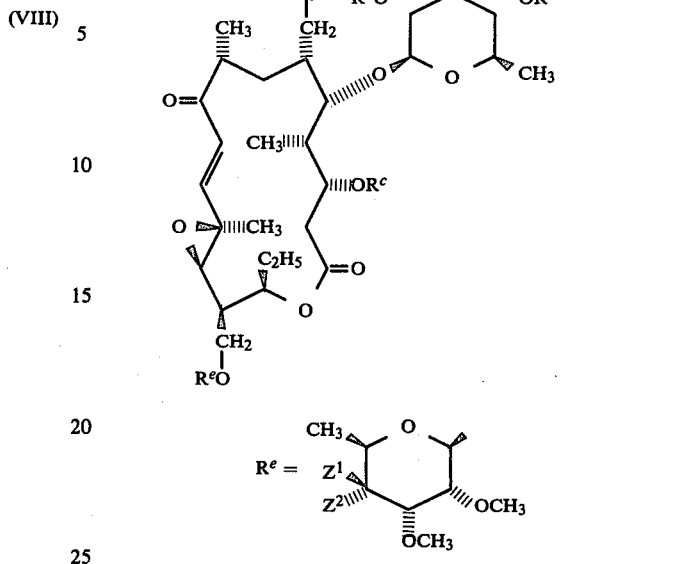

wherein:

| | $R^c$ | $R^d$ | Q | $Z^1/Z^2$ |
|---|---|---|---|---|
| a | H | H | CHO | H/OH |
| b | H | H | $CH(OR^7)_2$ | H/OH |
| c | H | $(C_2-C_6)$alkanoyl | $CH(OR^7)_2$ | H/OH |
| d | H | $(C_2-C_6)$alkanoyl | $CH(OR^7)_2$ | 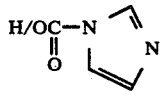 |
| e | TMS | $(C_2-C_6)$alkanoyl | $CH(OR^7)_2$ | 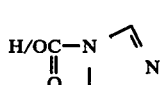 |
| f | TMS | $(C_2-C_6)$alkanoyl | $CH(OR^7)_2$ | H/OH |
| g | TMS | $(C_2-C_6)$alkanoyl | $CH(OR^7)_2$ | oxygen |
| h | H | $(C_2-C_6)$alkanoyl | $CH(OR^7)_2$ | oxygen |

(wherein $R^7$ is as previously defined and TMS = trimethylsilyl)

The conversions:

CP-56,064 (IXa)→(IXb)→(IXc)→(IXd)→(IXe)→
(IXf)→(IXg)→(IXh)

and:

CP-56,063 (Xa)→(Xb)→(Xc)→(Xd)→(Xe)→
(Xf)→(Xg)→(Xh)

are detailed in Preparations 4–11 below. The final stage selective removal of the oxidized sugar $R^e$ ($Z^1$ and $Z^2$ together=oxygen) is accomplished with ammonium acetate (molar excess) in a reaction-inert solvent such as lower secondary alcohol (2-propanol is well suited). Elevated temperature, e.g. 60°–100° C. is generally employed, the reflux temperature of 2-propanol being well-suited (see Method A below).

The pharmaceutically-acceptable acid addition salts of IIa are IIb are readily prepared by contacting the free base with a molar equivalent of the appropriate mineral or organic acid in an aqueous or organic solvent. If the salt directly precipitates, it is simply recovered by filtration. Otherwise it is isolated by concentration and/or addition of a nonsolvent.

The in vitro antibacterial activity of the compounds of the formulae (I) and (II) was demonstrated by measuring their minimum inhibitory concentrations (MIC's) in mcg/ml against a variety of microorganisms. The procedure which is followed is the one recommended by the International Collaborative Study on Antibiotic Sensitivity Testing [Ericcson and Sherris, Acta. Pathologica et Microbiologia Scandinav, Supp. 217, Sections A and B: 64–68 (1971)], and employs brain heart infusion (BHI) agar and the inocula replicating device. Overnight growth tubes are diluted 100 fold for use as the standard inoculum (20,000-10,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye. A comparison of the in vitro activity of various compounds of the formulae (I) and (II) with tylonolide is recorded in Table 1.

TABLE 1

In Vitro Antibacterial Activity of Compounds of the Formulae (I) and (II)

| Micro-organism | Minimum Inhibitory Concentration (MIC) mcg/ml | | | | | | | | |
|---|---|---|---|---|---|---|---|---|---|
| | (a) | (b) | (c) | (d) | (e) | (f) | (g) | (h) | (i) |
| Staph. aur. 5 | 0.78 | 0.78 | 0.10 | 0.39 | 0.20 | 3.12 | 0.78 | 0.78 | 0.78 |
| Staph. aur. 52 | 0.78 | 0.78 | 0.20 | 0.39 | 0.20 | 3.12 | 0.78 | 1.56 | 1.56 |
| Staph. aur. 400 | 1.56 | 0.78 | 0.20 | 1.56 | 0.20 | 3.12 | 0.39 | 1.56 | 1.56 |
| Staph. epi. 87 | 3.12 | — | — | — | — | — | 25 | — | — |
| Staph. epi. 111 | 1.56 | 1.56 | 0.10 | 0.78 | 0.20 | 1.56 | 0.20 | 0.78 | 0.78 |
| Staph. epi. 126 | 0.78 | 1.56 | 1.56 | 6.25 | 0.78 | 1.56 | 0.78 | 3.12 | 1.56 |
| Strep. faec. 6 | 0.78 | 0.39 | 0.10 | 3.12 | 0.39 | 6.25 | 0.78 | 3.12 | 0.39 |
| Strep. pneum. 12 | 0.10 | — | — | — | — | — | 0.02 | 0.39 | 0.20 |
| Strep. pyog. 203 | 0.39 | 0.20 | 0.05 | 0.10 | 0.10 | 0.39 | 0.39 | 0.20 | 0.20 |
| Bac. sub. 1 | — | 0.78 | 0.20 | 0.78 | 0.10 | 0.78 | 0.10 | — | — |
| E. coli 470 | 3.12 | — | — | — | — | — | 0.78 | 1.56 | 6.25 |
| Past. mult. 1 | 1.56 | 3.12 | 3.12 | — | 1.56 | 6.25 | 1.56 | 1.56 | 1.56 |
| Neiss. sic. | 6.25 | 1.56 | 0.78 | 0.78 | 0.39 | 3.12 | 1.56 | 12.5 | 1.56 |

(a) Micaminosyl tylonolide;
(b) Compound (I, A = $OSO_2(pCH_3C_6H_5)$, Y = oxygen, $R^1$ = H);
(c) Compound (I, A = $OSO_2(pCH_3C_6H_5)$, Y = $NN(CH_3)_2$, $R^1$ = H);
(d) Compound (I, A = I, Y = oxygen, $R^1$ = H)
(e) Compound (I, A = I, Y = $NN(CH_3)_2$, $R^1$ = H);
(f) Compound (I, A = $N(CH_3)_2$, Y = oxygen, $R^1$ = $CH_3CO$);
(g) Compound (I, A = Cl, Y = oxygen, $R^1$ = H);
(h) Compound (I, A = $N(CH_3)_2$, Y = oxygen, $R^1$ = H);
(i) Compound (II, A = $N(CH_2)_7$, Y = oxygen, $R^1$ = H).

Many compounds of the formulae (I) and (II) also exhibit in vivo activity against infections by sensitive bacteria, as summarized in Table 2. In determining such activity, acute experimental infections are produced in mice by the intraperitoneal inoculation of the mice with a standardized culture of the test organism suspended in 5 percent hog gastric mucin. Infection severity is standarized so that the mice receive at least one $LD_{100}$ dose of the organism ($LD_{100}$: the minimum inoculum of organism required to consistently kill 100 percent of the infected, nontreated control mice). The test compound is then subcutaneously or orally administered at various dosage levels to groups of infected mice. At the end of the test, the activity of the mixture is assessed by counting the number of survivors among treated animals at a given dose. Activity is expressed as the percentage of animals which survive at a given dose, or calculated as a $PD_{50}$ (dose which protects 50% of the animals from infection). A comparison of in vivo activity of various compounds of the formulae (I) and (II) is shown in Table 2.

TABLE 2

Subcutaneous In Vivo Acitivity of Compounds of the Formulae (I) and (II)[j]

| Compound | $PD_{50}$ (mg/kg) |
|---|---|
| (a) | 3.12 |
| (b) | 19 |
| (c) | 50 |
| (e) | greater than 50 |
| (g) | 13 |
| (h) | 2.4 |

(a)–(h) See Table 1 footnotes for identity of compounds
[j] All compounds tabulated showed oral $PD_{50}$ greater than 200 mg/kg.

For the treatment of systemic infections in animals, including man, caused by suseptible microorganisms, compounds of the formulae (I) and (II) are dosed at a level of 2.5–100 mg/kg per day, perferably 5–50 mg/kg/day, usually in divided doses. Variation in dosage will be made depending upon the individual and upon the susceptibility of the microorganism. These compounds are dosed orally or parenterally. The preferred route of administration is parenteral unless blood level determination following oral administration indicates good oral absorption. Such blood levels are readily determined using a bioassay based on standard dilution or disc-plate methods with a susceptible microorganism.

The susceptibility of microorganisms isolated in the clinics is routinely tested in clinical laboratories by the well-known disc-plate method. The preferred compound is that which shows the largest diameter zone of inhibition against the bacteria causing the infection to be treated.

Preparation of optimal dosage forms will be by methods well known in the pharmacists art. For oral administration, the compounds are formulated alone or in combination with pharmaceutical carriers such as inert solid diluents, aqueous solutions or various non-toxic organic solvents in such dosage forms as gelatin capsules, tablets, powders, lozenges, syrups and the like. Such carriers include water, ethanol, benzyl alcohol; glycerin, propylene glycol, vegetable oils, lactose, starches, talc, gelatins, gums and other well known carriers. The parenteral dosage forms required for the above systemic use are dissolved or suspended in a pharmaceutically-acceptable carrier such as water, saline, sesame oil, and the like. Agents which improve the suspendability and dispersion qualities can also be added.

For the topical treatment of superficial infections in animals, including man, caused by susceptible microorganisms, the antibacterial compounds are formulated by methods well known in the pharmacist's art into lotions, ointments, creams, salves, gels, or the like at concentrations in the range 5-200 mg/cc of the dosage form, preferably in the range 10-100 gm/cc. The dosage form is applied at the site of infection ad libitum, generally at least once a day.

When the antibacterial compounds of the present invention are used as preservations of biodegradable materials, they are simply blended with the biodegradable material at a concentration which is at least sufficient to inhibit the growth of the bacteria causing biodegradation. Routine serial dilution techniques can be used to determine the concentrations necessary to achieve the desired purpose.

When the antibacterial compounds of the present invention are used as growth promotants in domestic food animals, they are provided at low levels (e.g. 10 g to 100 g of compound per ton of feed). Blending of the compound with feed is usually accomplished in two stages, first in the preparation of a preblend (e.g. 10-100 g of compound blended with 10-20 lb of soybean mill run or the like), which is then blended with the feed at the time of milling.

When these compounds are used as industrial disinfectants, they are generally applied as dilute solutions to the surfaces which are to be disinfected.

The present invention is illustrated by the following examples. However, it should be understood that the invention is not limited to the specific details of these Examples. All temperatures are in °C. All unspecified temperatures are ambient (room) temperature. All tlc (thin layer chromatography) employs commercial silica gel plates containing U.V. detector. All solvent ratios are volume:volume. Solutions were dried over anhydrous $Na_2SO_4$. All solvents were stripped in vacuo.

METHOD A

SELECTIVE REMOVAL OF OXIDIZED MYCINOSE SUGAR

EXAMPLE A1

Compound (IV, $B=R^1=H$, $A^1=OH$, $R^6=CH_3CO$, $R^7=CH_3$) from Compound (Xh, $R^7=CH_3$, $R^d=CH_3CO$)

Title product of Preparation 11 (0.1 g, 0.1 mmole) was dissolved in 10 ml isopropanol. Ammonium acetate (0.1 g) was added and the mixture heated at reflux for one hour, then cooled and stripped to yield title product as a foam, 85 mg, tlc (ethyl acetate) $R_f 0.32$.

By the same method, the other products of Preparation 11 are converted to:

(IV, $B=R^1=H$, $A^1=OH$, $R^6=CH_3CO$, $R^7=C_2H_5$)
(IV, $B=R^1=H$, $A^1=OH$, $R^6=CH_3CO$, both $R^7$ together=—$(CH_2)_2$—)
(IV, $B=R^1=H$, $A^1=OH$, $R^6=CH_3(CH_2)_2CO$, $R^7=CH_3$)
(III, $B=R^1=H$, $A^1=OH$, $R^6=CH_3CO$, $R^7=CH_3$).

METHOD B

SELECTIVE DEACYLATION OF ACYLATED MYCAMINOSE SUGAR

EXAMPLE B1

Compound (IV, $B=R^1=R^6=H$, $A^1=OH$, $R^7=CH_3$) from Compound (IV, $B=R^1=H$, $A^1=OH$, $R^6=CH_3CO$, $R^7=CH_3$)

Title product of Example A1 (85 mg) was stirred for 18 hours in 2.5 ml methanol. The reaction mixture was stripped, dissolved in ethyl acetate and adjusted to pH 2.0 with dilute HCl. The aqueous phase was separated and extracted at pH 4.0, 5.5, 6.0, 6.5 and 10.0 with ethyl acetate. The pH was adjusted with dilute NaOH. Extracts at pH 6.0, 6.5 and 10.0 were combined and evaporated to yield title product, 69 mg; tlc (5:1 $CHCl_3$:methanol/trace $NH_4OH$) $R_f 0.42$; tlc (ethyl acetate) $R_f 0.03$.

By the same method the butyrate ester of Example A1 is converted to the same product, while the other esters of Example A1 are converted to:

(IV, $B=R^1=R^6=H$, $A^1=OH$, $R^7=C_2H_5$)
(IV, $B=R^1=R^6=H$, $A^1=OH$, both $R^7$ together=—$(CH_2)_2$—)
(III, $B=R^1=R^6=H$, $A^1=OH$, $R^7=CH_3$).

By the same method, isobutyrate, isovalerate and t-butyrate esters of Example C1 are converted to the same product, and the products of Example D1 are converted to the corresponding compounds of the formula (IV) wherein $B=R^1=R^6=H$, $R^7=CH_3$ and $A^1=OSO_2(pCH_3C_6H_4)$, $OSO_2C_6H_5$, $OSO_2(pClC_6H_4)$, $OSO_2(pCH_3OC_6H_4)$, $OSO_2(pBrC_6H_4)$, $OSO_2CH_2C_6H_5$, $OSO_2CH_3$, $OCOCH_3$, $OCO(CH_2)_2CH_3$, $OCOCH_2CH(CH_3)_2$, $OCOCH_2C(CH_3)_3$, $OCO(CH_2)_4CH_3$, $OCOC_6H_5$, $OCO(oC_2H_5OC_6H_4)$, $OCO(3-CH_3O-4-CH_3C_6H_3)$, $OCO(2,5-(CH_3)_2C_6H_3)$ or $OCO(CHCH_3(pClC_6H_4))$.

EXAMPLE B2

Compound (IV, $B=R^1=R^6=H$, $A^1=N(CH_2)_7$, $R^7=CH_3$) from Compound (IV, $B=R^1=H$, $A^1=$—$N(CH_2)_7$, $R^6=CH_3CO$, $R^7=CH_3$)

Title product of Example E1 (17 mg) was dissolved in methanol (2 ml), stirred 18 hours, and then evaporated to yield title product. The entire batch was used in Example F1.

By the same method, the other products of Example E1 are converted to the same compound; to the corresponding compounds of the formula (IV) wherein $B=R^1=R^6=H$, $R^7=CH_3$ and $A^1=$—$N(CH_3)_2$, —$N(C_2H_5)_2$, —$N(CH_3)(nC_3H_7)$, —$N(CH_3)(nC_4H_9)$, —$N(C_2H_5)(iC_3H_7)$, —$N(nC_3H_7)_2$, —$N(iC_3H_7)_2$, —$N(iC_3H_7)(tC_4H_9)$, —$N(nC_4H_9)_2$, —$N(nC_5H_{11})_2$, —$[N(CH(CH_3)CH_2CH(CH_3)_2]_2$, —$N(CH_2)_6$, —$N(CH_2)_5$, —$N(CH_2)_4$, or —$N(CH_2CH_2)_2O$; to compounds of the formula (IV) wherein $B=R^1=R^6=H$, $A^1=$—$N(CH_2)_7$ and $R^7=C_2H_5$ or both $R^7$ together=—$(CH_2)_2$—; or to a compound of the formula (III) wherein $B=R^1=R^6=H$, $A^1=$—$N(CH_2)_7$ and $R^7=CH_3$.

EXAMPLE B3

Compound (I, $A=OSO_2(pCH_3C_6H_4)$, $Y=NN(CH_3)_2$, $R^1=H$) from Compound (V, $A=OSO_2(pCH_3C_6H_4)$, $Y=NN(CH_3)_2$, $R^1=H$, $R^8=CH_3CO$)

The product of Examples D3/I2 (0.4 g) was stirred for 48 hours in 15 ml methanol, by which time tlc indicated reaction to be complete. Stripping gave title product, 0.35 g; tlc (ethyl acetate) $R_f 0.02$; tlc (3:1 $CHCl_3$:methanol) $R_f 0.52$.

By the same method, other compounds of Example D3 are converted to compounds of the formula (I) wherein $A=OSO_2(pCH_3C_6H_4)$, $R^1$ is H and Y is $NN(C_2H_5)_2$, $NN(CH_2)_4$, $NN(CH_2)_5$ or $NN(CH_2CH_2)_2O$.

EXAMPLE B4

Compound (I, A=I, Y=oxygen, $R^1$=H) from Compound (V, A=I, Y=oxygen, $R^1$=H, $R^8$=CH$_3$CO)

By the procedure of Example B3, aldehyde title product of Example J1 (120 mg) was converted to present title product, 90 mg; tlc (ethyl acetate) $R_f$ 0.02; tlc (3:1 CHCl$_3$:methanol) $R_f$ 0.51.

EXAMPLE B5

Compound (I, A=I, Y=NN(CH$_3$)$_2$, $R^1$=H) from Compound (V, A=I, Y=NN(CH$_3$)$_2$, $R^1$=H, $R^8$=CH$_3$CO)

By the procedure of Example B3, hydrazone title product of Example J1 (0.24 g) was converted to present title product, 0.2 g; tlc (ethyl acetate) $R_f$ 0.02; tlc (3:1 CHCl$_3$:methanol $R_f$ 0.44.

By the same method, other hydrazones of Example J1 are converted to compounds of the formula (I) wherein A=I, $R^1$=H, and Y=NN(C$_2$H$_5$)$_2$, NN(CH$_2$)$_4$, NN(CH$_2$)$_5$ or NN(CH$_2$CH$_2$)$_2$O.

EXAMPLE B6

Compound (III, B=$R^6$=H, $A^1$=OH, $R^1$=CH$_3$CO, $R^7$=CH$_3$) from Compound (III, B=H, $A^1$=OH, $R^1$=$R^6$=CH$_3$CO, $R^7$=CH$_3$)

Title product of Example L1 (1.3 g) was converted to present title product according to Example B3, 1.2 g, tlc (acetone) $R_f$ 0.25.

By the same method other compounds of Example L1 are converted to compounds of the formula (III) wherein B=$R^6$=H, $A^1$=OH, $R^7$=CH$_3$ and $R^1$=CH$_3$CH$_2$CO, CH$_3$(CH$_2$)$_2$CO, CH$_3$CH(CH$_3$)CO or CH$_3$CH$_2$CH(C$_2$H$_5$)CO; as well as the compounds:
(IV, B=$R^6$=H, $A^1$=OH, $R^1$=CH$_3$CO, $R^7$=CH$_3$) (I, A=OH, Y=oxygen, $R^1$=CH$_3$CO) (IV, B=$R^6$=H, $A^1$=OSO$_2$(pCH$_3$C$_6$H$_4$), $R^1$=CH$_3$CO, $R^7$=CH$_3$)
(I, A=OSO$_2$(pCH$_3$C$_6$H$_4$), Y=NN(CH$_3$)$_2$, $R^1$=CH$_3$CO).

EXAMPLE B7

Compound (III, B=$R^1$=$R^6$=H, $A^1$=OCOCH$_3$, $R^7$=CH$_3$) from Compound (III, B=$R^1$=H, $R^6$=CH$_3$CO, $A^1$=OCOCH$_3$, $R^7$=CH$_3$)

By the method of Example B3, title product of Example D4 (0.8 g) was converted to present title product, 0.8 g; tlc (ethyl acetate) $R_f$ 0.02; tlc (2:1 acetone:methanol) 0.38.

By the same method, the other products of Example D4 are converted to compounds of the formula (III) wherein B=$R^1$=$R^6$=H, $R^7$=CH$_3$ and $A^1$=OCOCH$_2$CH$_3$, OCOCH(CH$_3$)$_2$, OCO(CH$_2$)$_4$CH$_3$, OSO$_2$CH$_3$, OSO$_2$C$_6$H$_5$, OSO$_2$CH$_2$C$_6$H$_5$, OCOC$_6$H$_5$, OCO(mCH$_3$OC$_6$H$_4$), OCO(oFC$_6$H$_4$), OCO(2,5-Cl$_2$C$_6$H$_3$), OCO(3-F-4-CH$_3$C$_6$H$_3$) or OCOCH$_2$(pBrC$_6$H$_4$).

EXAMPLE B8

Compound (III, B=$R^1$=$R^6$=H, $A^1$=N-HSO$_2$(pCH$_3$C$_6$H$_5$), $R^7$=CH$_3$) from Compound (III, B=$R^1$=H, $A^1$=NHSO$_2$(pCH$_3$C$_6$H$_5$), $R^6$=CH$_3$CO, $R^7$=CH$_3$)

By the procedure of Example B2, title product of Example Q1 (0.46 g) was converted to present title product. The entire batch of product was used directly in the next step (Example F5).

By the same method, other products of Example Q1 are converted to compounds of the formula (III) wherein B=$R^1$=$R^6$=H, $R^7$=CH$_3$ and $A^1$=N-NSO$_2$(nC$_3$H$_7$), NHSO$_2$(iC$_3$H$_7$), NHSO$_2$(pClC$_6$H$_4$), NHSO$_2$CH$_2$C$_6$H$_5$, NHCOCH$_3$, NHCOCH$_2$CH(CH$_3$)$_2$, NHCO(CH$_2$)$_3$CH$_3$, NHCOC$_6$H$_5$, NHCO(mC$_2$H$_5$C$_6$H$_4$), NHCO(3,5-Cl$_2$C$_6$H$_3$ or NHCH$_2$(pCH$_3$OC$_6$H$_4$); compound (IV, B=$R^1$=$R^6$=H, $A^1$=NHSO$_2$(pCH$_3$C$_6$H$_4$), $R^7$=CH$_3$); or compound (I, A=NHSO$_2$(pCH$_3$C$_6$H$_4$), Y=oxygen, $R^1$=H).

EXAMPLE B9

Compound (I, A=Cl, Y=oxygen, $R^1$=H) from Compound (V, A=Cl, Y=oxygen, $R^1$=H, $R^8$=CH$_3$CO)

Using a 24 hour reaction time, the entire batch of title product from Example F6 (0.11 g) was converted to present title product (crude), purified by taking into water and ethyl acetate, adjusting to pH 10.0 with dilute NaOH, and separating, drying and stripping the organic layer, 0.1 g, tlc (3:1 CHCl$_3$:methanol) $R_f$ 0.30.

METHOD C

SELECTIVE ACYLATION OF MYCAMINOSE SUGAR

EXAMPLE C1

Compound (IV, B=$R^1$=H, $A^1$=OH, $R^6$=CH$_3$CO, $R^7$=CH$_3$) from Compound (IV, B=$R^1$=$R^6$=H, $A^1$=OH, $R^7$=CH$_3$)

Title product of Example B1 (44 mg, 0.067 mmole) and acetic anhydride (0.02 ml, 0.26 mmole) were combined in 5 ml ethyl acetate and stirred for 18 hours by which time tlc indicated reaction was complete. The mixture was then diluted with 5 ml H$_2$O, stirred for 0.5 hour and adjusted to pH 9.5 with dilute NaOH. The organic layer was separated, dried and stripped to yield title product, 44mg, tlc (ethyl acetate) $R_f$ 0.3–0.42.

By the same method other compounds of Example B1 are converted to:
(IV, B=$R^1$=H, $A^1$=OH, $R^6$=CH$_3$CO, $R^7$=C$_2$H$_5$)
(IV, B=$R^1$=H, $A^1$=OH, $R^6$=CH$_3$CO, both $R^7$ taken together =—(CH$_2$)$_2$—)
(III, B=$R^1$=H, $A^1$=OH, $R^6$=CH$_3$CO, $R^7$=CH$_3$).

Substituting an equivalent amount of the appropriate acid anhydride for acetic anhydride in this process produces compounds of the formula (IV) wherein B=$R^1$=H, $A^1$=OH, $R^7$=CH$_3$ and $R^6$ is CH$_3$CH$_2$CO, CH(CH$_3$)$_2$CO, CH(CH$_3$)$_2$CH$_2$CO or C(CH$_3$)$_3$CO.

EXAMPLE C2

Compound (III, B=$R^1$=H, $A^1$=OH, $R^6$=CH$_3$CO, $R^7$=CH$_3$) from Compound (III, B=$R^1$=$R^6$=H, $A^1$=OH, $R^7$=CH$_3$)

Title product of Example G1 (12.8 g, 19.9 mmole), CH$_2$Cl$_3$ (100 ml) and acetic anhydride (7.5 ml, 79.6 mmole) were combined and stirred for one hour, by which time tlc indicated reaction was complete. The mixture was diluted with 100 ml H$_2$O, adjusted to pH 10.0 with 1N NaOH and the organic layer separated, dried and stripped to yield title product as a foam, 14 g; tlc (3:1 CHCl$_3$:methanol) $R_f$ 0.88; tlc (ethyl acetate) $R_f$ 0.43; tlc (ether) $R_f$ 0.27.

By the same method other compounds of Example G1 are converted to corresponding compounds of the formula (III) wherein B=$R^1$=H, $A^1$=OH, $R^6$=CH$_3$CO and $R^7$=nC$_3$H$_7$ or both $R^7$ together =—CH$_2$CH(CH$_3$)—; or of the formula (IV) wherein B=$R^1$=H, $A^1$=OH, $R^6$=CH$_3$CO and $R^7$=CH$_3$ or nC$_3$H$_7$, or both $R^7$ together =—(CH$_2$CH(CH$_3$)—.

EXAMPLE C3

Compound (V, A=OH, Y=oxygen, $R^1$=H, $R^8$=CH$_3$CO) by Acetylation of Desmycarosyl Desmycinosyl Tylosin (Desmycinosyl Tolonide; Mycaminosyl Tylonolide)

According to the method of Example C2, mycaminosyl tylonolide [Omura et al., Tetrahedron Letters No. 12, pp. 1045–1048, 1977; tlc (3:1 CHCl$_3$:methanol) $R_f$ 0.3; 35.5 g, 0.059 mole] was reacted with acetic anhydride and product isolated as a foam, 42.5 g; tlc (3:1 CHCl$_3$:methanol) $R_f$ 0.78; tlc (ethyl acetate) $R_f$ 0.05.

By the same method compound (II, A=OH, Y=oxygen, $R^1$=H) of Example F1 is converted to compound (VI, A=OH, Y=oxygen, $R^1$=H, $R^8$=CH$_3$CO).

METHOD D

SELECTIVE ACYLATION OF HYDROXYMETHYL SIDE CHAIN

EXAMPLE D1

Compound (IV, B=$R^1$=H, $A^1$=OSO$_2$(pCH$_3$C$_6$H$_4$), $R^6$=CH$_3$CO, $R^7$=CH$_3$) from Compound (IV, B=$R^1$=H, $A^1$=OH, $R^6$=CH$_3$CO, $R^7$=CH$_3$)

Title product of Example A1 or C1 (44 mg, 0.06 mmole), p-toluenesulfonyl chloride (28 mg, 0.15 mmole), triethylamine (0.02 ml, 0.15 mmole) and a catalytic amount of 4-dimethylaminopyridine (10 mg) were combined in 5 ml CH$_2$Cl$_2$ and stirred 18 hours, by which time tlc indicated complete reaction. The reaction mixture was stripped to a foam, which was dissolved in ethyl acetate, diluted with water, adjusted to pH 2.5 with dilute HCl and the layers separated. The organic layer was combined with fresh H$_2$O, adjusted to pH 9.5 with dilute NaOH and the organic layer reseparated, dried and stripped to yield title product, 50 mg, tlc (ethyl acetate) $R_f$ 0.74.

Substituting an equivalent of the appropriate sulfonyl chloride or carboxylic acid chloride for p-toluenesulfonyl chloride in this process produces the corresponding compounds of the formula (IV) wherein B=$R^1$=H, $R^6$=CH$_3$CO, $R^7$=CH$_3$ and $A^1$=OSO$_2$C$_6$H$_5$, OSO$_2$(pClC$_6$H$_4$), OSO$_2$(pCH$_3$OC$_6$H$_4$), OSO$_2$(pBrC$_6$H$_4$), OSO$_2$CH$_2$C$_6$H$_5$, OSO$_2$CH$_3$, OCOCH$_3$, OCO(CH$_2$)$_2$CH$_3$, OCOCH$_2$CH(CH$_3$)$_2$, OCOCH$_2$C(CH$_3$)$_3$, OCO(CH$_2$)$_4$CH$_3$, OCOC$_6$H$_5$, OCO(oC$_2$H$_5$OC$_6$H$_4$), OCO(3-CH$_3$O-4-CH$_3$C$_6$H$_3$), OCO(2,5-(CH$_3$)$_2$C$_6$H$_3$) or OCOCHCH$_3$(pClC$_6$H$_4$).

By the same method, other compounds of Example C1, as appropriate, are converted to compounds of the formula (IV) wherein B=$R^1$=H, $A^1$=OSO$_2$(pCH$_3$C$_6$H$_4$), $R^7$=CH$_3$ and $R^6$=CH$_3$CH$_2$CO, CH(CH$_3$)$_2$CO, CH(CH$_3$)$_2$CH$_2$CO or C(CH$_3$)$_3$CO; to compounds of the formula (IV) wherein B=$R^1$=H, $A^1$=OSO$_2$(pCH$_3$C$_6$H$_4$), $R^6$=CH$_3$CO and $R^7$=C$_2$H$_5$, or both $R^7$ are taken together and are (CH$_2$)$_2$; or to a compound of the formula (III) wherein B=$R^1$=H, $A^1$=OSO$_2$(pCH$_3$C$_6$H$_4$), $R^6$=CH$_3$CO and $R^7$=CH$_3$.

EXAMPLE D2

Compound (V, A=OSO$_2$(pCH$_3$C$_6$H$_4$), Y=oxygen, $R^1$=H, $R^8$=CH$_3$CO) from Compound (V, A=OH, Y=oxygen, $R^1$=H, $R^8$=CH$_3$CO)

Title product of Example C3 (5.3 g, 7.8 mmoles), p-toluenesulfonyl chloride (24 mmole) and triethylamine (3.4 ml, 25 mmole) were combined in 150 ml CH$_2$Cl$_2$ and stirred 18 hours, by which time tlc indicated reaction complete. The mixture was poured into 150 ml water, adjusted to pH 10.0 with K$_2$CO$_3$ and the organic layer separated, stripped to a first foam, taken up in 50 ml ether, precipitated with 300 ml hexane, and tacky solids recovered by decantation. The tacky solids were triturated with fresh hexane, taken up in ethyl acetate and restripped to yield title product as a second foam, 5.0 g, tlc (ethyl acetate) $R_f$ 0.63.

EXAMPLE D3

Compound (V, A=OSO$_2$(pCH$_3$C$_6$H$_4$), Y=NN(CH$_3$)$_2$, $R^1$=H, $R^8$=CH$_3$CO) from Compound (V, A=OH, Y=NN(CH$_3$)$_2$, $R^1$=H, $R^8$=CH$_3$CO)

By the procedure of Example D2, using 1N NaOH for pH adjustment, title product of Example I1 (8.2 g, 11.3 mmoles) was converted to crude title product (11.7 g, corresponding to the first foam of that Example). The crude product was chromatograhed on 100 g silica gel (30 mm diameter column) with 3:1 CHCl$_3$:acetone as eluant. After developing the column with 100 ml of eluant, 8 ml fractions were collected. Fractions 30–70 were combined and stripped to yield title product, 3.5 g; tlc (ethyl acetate) $R_f$ 0.46; tlc (3:1 CHCl$_3$:methanol) $R_f$ 0.36; tlc (ether) $R_f$ 0.11. Fractions 20–30 gave 1.7 g additional title product contaminated with p-toluenesulfonyl chloride.

By the same method, the other compounds of Example I1 are converted to compounds of the formula (V) whrerein A=OSO$_2$(pCH$_3$C$_6$H$_4$), $R^1$=H, $R^2$=CH$_3$CO and Y=NN(C$_2$H$_5$)$_2$, NN(CH$_2$)$_4$, NN(CH$_2$)$_5$, or NN(CH$_2$CH$_2$)$_2$O.

EXAMPLE D4

Compound (III, B=$R^1$=H, $A^1$=OCOCH$_3$, $R^6$=CH$_3$CO, $R^7$=CH$_3$) from Compound (III, B=$R^1$=H, $A^1$=OH, $R^6$=CH$_3$CO, $R^7$=CH$_3$)

Title product of Example C2 (1.5 g, 2.0 mmole) was dissolved in 25 ml ethyl acetate. Acetic anhydride (0.2 ml, 2.2 mmoles) and then triethylamine (0.3 ml, 2.2 mmoles) were added and the mixture stirred 18 hours by which time tlc indicated reaction about ⅔ complete. Additional acetic anhydride (0.1 ml) and triethylamine (0.15 ml), together with 10 mg 4-dimethylaminopyridine, were added. After 3 hours, tlc indicated reaction was complete. The reaction was poured into 50 ml of water, stirred to decompose excess acetic anhydride while adjusting to pH 10.0 with 1N NaOH. The organic phase was separated, dried, stripped to a foam (1.4 g) and chromatographed on 30 g silica gel in a 25 mm diameter column, using ether as eluant and collecting 7 ml fractions. Fractions 40–110 were combined and stripped to yield title product, 0.8 g; tlc (ethyl acetate) $R_f$ 0.78; tlc (2:1 acetone:methanol) $R_f$ 0.95.

The same method, substituting an equivalent of the appropriate acid anhydride or acid chloride for acetic anhydride, yields additional compounds of the formula (III) wherein B=$R^1$=H, $R^6$=CH$_3$CO, $R^7$=CH$_3$ and $A^1$=OCOCH$_2$CH$_3$, OCOCH(CH$_3$)$_2$, OCO(CH$_2$)$_4$CH$_3$, OSO$_2$CH$_3$, OSO$_2$C$_6$H$_5$, OSO$_2$CH$_2$C$_6$H$_5$, OCOC$_6$H$_5$, OCO(mCH$_3$OC$_6$H$_4$), OCO(oFC$_6$H$_4$), OCO(2,5-CL$_2$C$_6$H$_3$), OCO(3-F-4-CH$_3$C$_6$H$_3$), or OCOCH$_2$(pBrC$_6$H$_5$).

EXAMPLE D5

Compound (III, B=$R^1$=H, $A^1$=OSO$_2$(pCH$_3$C$_6$H$_4$), $R^6$=CH$_3$CO, $R^7$=CH$_3$) from Compound (III, B=$R^1$=H, $A^1$=OH, $R^6$=CH$_3$CO, $R^7$=CH$_3$)

Title product of Example C2 (14.0 g, 19 mole), p-toluenesulfonyl chloride (14.4 g, 76 mmole), triethylamine (10.5 ml, 76 mmole) and 4-dimethyl- aminopyridine (0.23 g, 1.9 mmole) were combined in 150 ml $CH_2Cl_2$, stirred to 1.5 hours (by which time tlc indicated complete reaction), poured into 150 ml $H_2O$ and stirred 18 hours to decompose excess acid chloride. The organic phase was separated, dried and stripped to yield title product as a foam, 16.0 g, tlc (ether) $R_f$ 0.32.

METHOD E

REPLACEMENT OF SULFONYLOXY WITH $R^2R^3N$

EXAMPLE E1

Compound (IV, $B=R^1=H$, $A^1=-N(CH_2)_7$, $R^6=CH_3CO$, $R^7=CH_3$) from Compound (IV, $B=R^1=H$, $A^1=OSO_2(pCH_3C_6H_4)$, $R^7=CH_3$)

Title product of Example D1 (50 mg, 0.056 mmole), perhydroazocine (heptamethylenimine, 0.09 ml, 0.6 mmole) and sodium iodide (9 mg, 0.06 mmole) were combined in 3 ml acetone and refluxed for 24 hours. The reaction mixture was diluted with ethyl acetate and water, the pH adjusted to 2.0 with dilute HCl. The aqueous phase was separated and extracted with fresh ethyl acetate at pH 4.0, 6.0 and 10.0 (pH adjusted with dilute NaOH). Extracts containing product by tlc were combined and evaporated to yield title product, 17 mg, tlc (ethyl acetate) $R_f$ 0.23.

Substituting perhydroazocine with an equivalent of the appropriate amine yields additional products of the formula (IV) wherein $B=R^1=H$, $R^6=CH_3CO$, $R^7=CH_3$ and $A^1=-N(CH_3)_2$, $-N(C_2H_5)_2$, $-N(CH_3)(nC_3H_7)$, $-N(CH_3)(nC_4H_9)$, $-N(C_2H_5)(iC_3H_7)$, $-N(nC_3H_7)_2$, $-N(iC_3H_7)_2$, $-N(iC_3H_7)(tC_4H_9)$, $-N(nC_4H_9)_2$, $-N(nC_5H_{11})_2$, $-N(C_2H_5)[CH(CH_3)CH_2CH(CH_3)_2]_2$, $-N(CH_2)_6$, $-N(CH_2)_5$, $-N(CH_2)_4$ or $-N(CH_2CH_2)_2O$.

By the same method, the other sulfonate esters of Example D1, as appropriate, are converted to the same product; to a compound of the formula (IV) wherein $B=R^1=H$, $A^1=-N(CH_2)_7$, $R^7=CH_3$ and $R^6=CH_3CH_2CO$, $CH(CH_3)_2CO$, $CH(CH_3)_2CH_2CO$ or $C(CH_3)_3CO$; to a compound of the formula (IV) wherein $B=R^1=H$, $A^1=-N(CH_2)_7$, $R^6=CH_3CO$ and $R^7=C_2H_5$ or both $R^7$ taken together $=-(CH_2)_2-$; or to a compound of the formula (III) wherein $B=R^1=H$, $A^1=-N(CH_2)_7$, $R^6=CH_3CO$ and $R^7=CH_3$.

METHOD F

DEACETALIZATION

EXAMPLE F1

Compound (II, $A=-N(CH_2)_7$, $Y=$oxygen, $R^1=H$) from Compound (IV, $B=R^1=R^6=H$, $A^1=-N(CH_2)_7$, $R^7=CH_3$)

Title product of Example B2, the entire batch was dissolved in 4 ml 1:1 $CH_3CN:H_2O$. A single drop of $F_2CHCO_2H$ was added and the solution stirred 18 hours. Two more drops of $F_2CHCOOH$ were added and the reaction mixture was stirred an additional 18 hours, then diluted with $H_2O$ and ethyl acetate, the pH was adjusted to 8.5 with dilute NaOH and the organic layer separated, dried and stripped to yield 7 g of title product. Product was further purified by taking up in 30 ml each ethyl acetate and $H_2O$, adjusting to pH 2.0 with dilute HCl and separating the aqueous phase. The aqueous phase, adjusting pH with dilute NaOH, was extracted at pH 4.0, 5.5 and 7.0 with 30 ml of fresh ethyl acetate at each pH value. The pH 7.0 extract was washed with saturated $NaHCO_3$ and stripped to yield purified title product, 3.7 mg, tlc (5:1 $CHCl_3$:methanol/trace $NH_4OH$) $R_f$ 0.44.

By the same method the other compounds of Example B2 are converted to the same compound; to the corresponding compounds of the formula (II) wherein Y is oxygen, $R^1$ is H and A is $-N(CH_3)_2$, $-N(C_2H_5)_2$, $-N(CH_3)(nC_3H_7)$, $-N(CH_3)(nC_4H_9)$, $-N(C_2H_5)(iC_3H_7)$, $-N(nC_3H_7)_2$, $-N(iC_3H_7)_2$, $-N(iC_3H_7)(tC_4H_9)$, $-N(nC_4H_9)_2$, $-N(nC_5H_{11})_2$, $-N[CH(CH_3)CH_2CH(CH_3)_2]_2$, $-N(CH_2)_6$, $-N(CH_2)_5$, $-N(CH_2)_4$, or $-N(CH_2CH_2)_2O$; or to compound of the formula (I) wherein A is $-N(CH_2)_7$, Y is oxygen and $R^1$ is H.

By the same method the products of Example B1 are converted to a compound of the formula (II) wherein Y is oxygen, $R^1$ is hydrogen and A is OH, $OSO_2(pCH_3C_6H_4)$, $OSO_2C_6H_5$, $OSO_2(pClC_6H_4)$, $OSO_2(pCH_3OC_6H_4)$, $OSO_2(pBrC_6H_4)$, $OSO_2CH_2C_6H_5$, $OSO_2CH_3$, $OCOCH_3$, $OCO(CH_2)_2CH_3$, $OCOCH_2CH(CH_3)_2$, $OCOCH_2C(CH_3)_3$, $OCO(CH_2)_4CH_3$, $OCOC_6H_5$, $OCO(oC_2H_5OC_6H_4)$, $OCO(3-CH_3O-4-CH_3C_6H_3)$, $OCO(2,5-(CH_3)_2C_6H_3)$ or $OCOCHCH_3(pClC_6H_4)$; or to a compound of the formula (I) wherein Y is oxygen, $R^2$ is hydrogen and A is OH.

EXAMPLE F2

Compound (I, $A=OH$, $Y=$oxygen, $R^1=CH_3CO$) from Compound (III, $B=R^6=H$, $A^1=OH$, $R^1=CH_3CO$, $R^7=CH_3$)

Title product of Example B6 (1.2 g, 1.7 mmole) and $F_2CHCO_2H$ (0.28 ml, 4.4 mmoles) were combined in 50 ml 1:1 $CH_3CN:H_2O$, stirred overnight, then poured into 50 ml each of $H_2O$ and ethyl acetate and the pH adjusted to 10.0 with 1N NaOH. The organic phase was separated, dried and stripped to yield title product as a foam, 0.95 g, tlc (acetone) $R_f$ 0.25.

By the same method, other compounds of Example B6 are converted to compounds of the formula (I) wherein $A=OH$, $Y=$oxygen and $R^1=CH_3CH_2CO$, $CH_3(CH_2)_2CO$, $CH_3CH(CH_3)CO$ or $CH_3CH_2CH(C_2H_5)CO$; compound (II, $A=OH$, $Y=$oxygen, $R^1=CH_3CO$); and compound (II, $A=OSO_2(pCH_3C_6H_4)$, $R^1=CH_3CO$).

EXAMPLE F3

Compound (I, $A=N(CH_3)_2$, $Y=$oxygen, $R^1=CH_3CO$) from Compound (III, $B=R^6=H$, $A^1=N(CH_3)_2$, $R^1=CH_3CO$, $R^7=CH_3$)

Title product of Example N1 (0.1 g) was dissolved in 20 ml 1:1 $H_2O$:ethyl acetate and the pH adjusted to 2.0 with 1N HCl. After stirring 4 hours, the pH was adjusted to 1.7 and stirring continued 1.5 hours. To isolate, the pH was adjusted to 10.0 with 1N NaOH. The aqueous phase was separated and extracted with 10 ml fresh ethyl acetate. The two organic layers were combined, dried and stripped to yield title product, 80 mg, tlc (3:1 $CHCl_3$:methanol) $R_f$ 0.27.

By the same method, other compounds of Example N1 are converted to compounds of the formula (I) wherein $A=N(CH_3)_2$, $Y=$oxygen and $R^1=CH_3CH_2CO$, $CH_3(CH_2)_2CO$, $CH_3CH(CH_3)CO$, or $CH_3CH_2CH(C_2H_5)CO$; compound (II, $A=N(CH_3)_2$, $Y=$oxygen, $R^1=CH_3CO$) or compound of the formula (I) wherein $Y=$oxygen, $R^1=CH_3CO$ and $A=N(C_2H_5)_2$, $N(iC_3H_7)_2$, $N(CH_3)(nC_4H_9)$, $N(CH_2)_7$, $N(CH_2)_4$ or $N(CH_2CH_2)_2O$.

EXAMPLE F4

Compound (I, $A=OCOCH_3$, $Y=oxygen$, $R^1=H$) from Compound (III, $B=R^1=R^6=H$, $A^1=OCOCH_3$, $R^7=CH_3$)

By the procedure of Example F2 title product of Example B7 (0.8 g, 1.2 mmoles) was converted to present title product, 0.5 g, tlc (2:1 acetone:methanol) $R_f$ 0.40.

By the same procedure, the other compounds of Example B7 are converted to compounds of the formula (I) wherein $Y=oxygen$, $R^1=H$ and $A^1=OCOCH_2CH_3$, $OCOCH(CH_3)_2$, $OCO(CH_2)_4CH_3$, $OSO_2CH_3$, $OSO_2C_6H_5$, $OSO_2CH_2C_6H_5$, $OCOC_6H_5$, $OCO(mCH_3OC_6H_4)$, $OCO(oFC_6H_4)$, $OCO(2,5-Cl_2C_6H_3)$, $OCO(3-F-4-CH_3C_6H_3)$ or $OCOCH_2(pBrC_6H_4)$.

EXAMPLE F5

Compound (I, $A=NHSO_2(pCH_3C_6H_4)$, $Y=oxygen$, $R^1=H$) from Compound (III, $B=R^1=R^6=H$, $A^1=NHSO_2(pCH_3C_6H_4)$, $R^7=CH_3$)

By the method of Example F2, using a reaction time of 25 hours, the entire batch of title product of Example B8 was converted to present title product, 0.26 g; tlc (ether) $R_f$ 0.02; tlc (1:1 acetone:methanol) 0.55.

By the same method other compounds of Example B8 are converted to compounds of the formula (I) wherein $Y=oxygen$, $R^1=H$, and $A=NHSO_2(nC_3H_7)$, $NHSO_2(iC_3H_7)$, $NHSO_2(pClC_6H_4)$, $NHSO_2CH_2C_6H_5$, $NHCOCH_3$, $NHCOCH_2CH(CH_3)_2$, $NHCO(CH_2)_3CH_3$, $NHCOC_6H_5$, $NHCO(mC_2H_5C_6H_4)$, $NHCO(3,5-Cl_2C_6H_3)$ or $NH(pCH_3OC_6H_4)$; or compound (II, $A^1=NHSO_2(pCH_3C_6H_4)$, $Y=oxygen$, $R^1=H$).

EXAMPLE F6

Compound (V, $A=Cl$, $Y=oxygen$, $R^1=H$, $R^8=CH_3CO$) from Compound (III, $B=R^1=H$, $A^1=Cl$, $R^6=CH_3CO$, $R^7=CH_3$)

By the method of Example F5, title product of Example H1 (0.13 g, 0.17 mmole) was converted to present title product (0.11 g), the entire batch used in the next step (Example B9).

METHOD G

ACETAL FORMATION

EXAMPLE G1

Compound (III, $B=R^1=R^6=H$, $A^1=OH$, $R^7=CH_3$) by Dimethylacetalization of Mycaminosyl Tylonolide Mycaminosyl tylonolide (see Example C3; 14.0 g, 23.4 mmoles), methanol (150 ml) and methanolic HCl (1.87M, 23.8 ml, 46.8 mmoles) were combined and stirred for two hours, by which time tlc indicated complete reaction. The reaction mixture was added to 300 ml each of H2O and ethyl acetate, the pH was adjusted to 10.0 with 1N NaOH and the organic phase separated, washed 1×150 ml saturated NaCl, dried and stripped to yield title product as a foam, 12.8 g, tlc (3:1 CHCl3:methanol) $R_f$ 0.44.

Substituting, respectively, an equal volume of 1-propanol or 1,2-propandiol for methanol and an equivalent of 1-propanolic HCl or 1,2-propandiolic HCl for methanolic HCl yields the corresponding acetals of the formula (III) wherein $B=R^1=R^6=H$, $A^1=OH$ and $R^7$ is n-propyl or both $R^7$ together = $-CH_2CH(CH_3)-$.

By these same processes, compound of the formula (II), wherein $Y=oxygen$, $R^1$ is hydrogen and A is OH (Example F1) is converted to the corresponding acetals of the formula (IV), wherein $B=R^1=R^6=H$, $A^1=OH$ and $R^7$ is methyl or n-propyl, or both $R^7$ together = $-CH_2CH(CH_3)-$.

METHOD H

SELECTIVE REPLACEMENT OF HYDROXYMETHYL WITH HALOMETHYL

EXAMPLE H1

Compound (III, $B=R^1=H$, $A^1=Cl$, $R^6=CH_3CO$, $R^7=CH_3$) from Compound (III, $B=R^1=H$, $A^1=OH$, $R^6=CH_3CO$, $R^7=CH_3$)

Title product of Example C2 (0.45 g, 0.62 mmole), CCl4 (10 ml) and $(C_6H_5)_3P$ (0.4 g, 1.5 mmoles) were combined and refluxed for 18 hours, by which time tlc indicated reaction was complete. The reaction was stripped of solvent, the resulting foam triturated with ether and the ether stripped to a second foam (0.59 g). The second foam was chromatographed on 10 g silica gel, collecting 120×2 ml fractions with CHCl3 as eluant and monitoring by tlc. Fractions 35 and 36 were combined and stripped to yield purified title product, 0.15 g; tlc (ethyl acetate) $R_f$ 0.67; tlc (3:1 CHCl3:methanol) $R_f$ 0.92.

By the same method, other products of Example C2 are converted to corresponding compounds of the formula (III) wherein $B=R^1=H$, $A^1=Cl$, $R^6=CH_3CO$ and $R^7=nC_3H_7$ or both $R^7$ together = $-CH_2CH(CH_3)-$; or of the formula IV wherein $B=R^1=H$, $A^1=Cl$, $R^6=CH_3CO$ and $R^7=CH_3$ or n-$C_3H_7$, or both $R^7$ taken together = $-CH_2CH(CH_3)-$.

METHOD I

HYDRAZONE FORMATION

EXAMPLE I1

Compound (V, $A=OH$, $Y=NN(CH_3)_2$, $R^1=H$, $R^8=CH_3CO$) from Compound (V, $A=OH$, $Y=oxygen$, $R^1=H$, $R^8=CH_3CO$)

Title product of Example C3 (10.0 g, 14.7 mmole), 1,1-dimethylhydrazine (1.2 ml, 16 mmole) and acetic acid (0.1 ml, 1.5 mmole) were combined in 50 ml of 2-propanol, stirred 18 hours, then quenched into 150 ml each H2O and ethyl acetate, and the organic layer separated, dried and stripped to yield title product as a foam, 8.2 g, tlc (ethyl acetate) $R_f$ 0.23.

The same method, substituting an equivalent of the appropriate hydrazine for 1,1-dimethylhydrazine, yields additional compounds of the formula (V), wherein $A=OH$, $R^1=H$, $R^8=CH_3CO$ and $Y=NN(C_2H_5)_2$, $NN(CH_2)_4$, $NN(CH_2)_5$, or $NN(CH_2CH_2)_2O$.

EXAMPLE I2

Compound (V, $A=OSO_2(pCH_3C_6H_4)$, $Y=NN(CH_3)_2$, $R^1=H$, $R^8=CH_3CO$) from Compound (V, $A=OSO_2(pCH_3C_6H_4)$, $Y=oxygen$, $R^1=H$, $R^8=CH_3CO$)

Using a reaction temperature of 40°–50° and adjusting the aqueous phase to pH 10.0 with 1N NaOH before separating the organic phase in work-up, the procedure of Example I1 was used to convert title product of Example D2 (4.7 g, 5.6 mmole) to present title product, further purified by ether repulp, 3.2 g, identical with the product of Example D3.

METHOD J

REPLACEMENT OF SULFONYLOXY WITH HALIDE

EXAMPLE J1

Compound (V, A=I, Y=NN(CH$_3$)$_2$, R$^1$=H, R$^8$=CH$_3$CO) and Compound (V, A=I, Y=oxygen, R$^1$=H, R$^8$=CH$_3$CO) from Compound (V, A=OSO$_2$(pCH$_3$C$_6$H$_4$), Y=NN(CH$_3$)$_2$, R$^1$=H, R$^8$=CH$_3$CO)

Title product of Examples D3/I2 (1.0 g, 0.32 mmole), 3 ml 10% NaI and acetone (20 ml) were heated to reflux for 18 hours, by which time tlc indicated starting material to be completely consumed. The reaction mixture was poured into 60 ml each H$_2$O and ethyl acetate, and the organic phase separated, dried, stripped to a foam, the foam taken up in ether, filtered from insoluble material (0.15 g) and the filtrate restripped to a second foam, 0.7 g, which was chromatographed on 25 g silica gel in a 20 mm diameter column with ether as eluant, collecting 5 ml fractions. Fractions 28–55 were combined and stripped to yield the title aldehyde, 120 mg; tlc (ethyl acetate) R$_f$ 0.70; tlc (ether) R$_f$ 0.45. Fractions 65–150 were combined and stripped to yield title hydrazone, 240 mg; tlc (ethyl acetate) R$_f$ 0.47; tlc (ether) R$_f$ 0.22.

By the same method, other compounds of Example D3 are converted to the same aldehyde and hydrazones of the formula (V) wherein A=I, R$^1$=H, R$^8$=CH$_3$CO and Y is NN(C$_2$H$_5$)$_2$, NN(CH$_2$)$_4$, NN(CH$_2$)$_5$ or NN(CH$_2$CH$_2$)$_2$O.

METHOD K

HYDRAZONE TO ALDEHYDE (See Example J1)

METHOD L

SELECTIVE ACYLATION OF C-3 SECONDARY HYDROXYL GROUP

EXAMPLE L1

Compound (III, B=H, A$^1$=OH, R$^1$=R$^6$=CH$_3$CO, R$^7$=CH$_3$) from Compound (III, B=R$^1$=H, A$^1$=OH, R$^6$=CH$_3$CO, R$^7$=CH$_3$)

Title product of Example C2 (4.0 g, 5.5 mmoles), carbonyldiimidazole (0.98 g, 6.0 mmoles) were combined with 50 ml CH$_2$Cl$_2$, stirred 4 hours (by which time tlc indicated reaction was complete), washed with H$_2$O, dried and stripped to yield intermediate in which the hydroxymethyl group of starting material is protected with a 1-imidazolylcarbonyl group, 4.3 g, tlc (ethyl acetate) R$_f$ 0.25.

This hydroxymethyl protected intermediate (1.0 g, 1.2 mmoles, acetic anhydride (0.23 ml, 2.4 mmoles, triethylamine (0.33 ml, 2.4 mmoles and 4-dimethylaminopyridine (10 mg) were combined in 10 ml ethyl acetate, stirred 18 hours (by which time tlc indicated reaction was complete) and then combined with 15 ml H$_2$O, the pH adjusted to 10.0 with 1N NaOH, and the layers separated. The aqueous phase was extracted 2×20 ml ethyl acetate. The three organic layers were combined, dried and stripped to yield a second intermediate in which the C-3 hydroxy group is acetylated and the hydroxymethyl group remains protected, 0.9 g, tlc (ethyl acetate) R$_f$ 0.28.

The second intermediate (0.9 g, 1 mmole), K$_2$CO$_3$ (0.14 g, 1.0 mmole) and 30 ml of 2:1 acetone:H$_2$O were combined and the solution stirred 2 hours, then poured into 50 ml each of H$_2$O and ethyl acetate and the layers separated. The aqueous layer was extracted 2×20 ml ethyl acetate. The three organic layers were combined, dried and stripped to yield title product as a foam, 0.76 g; tlc (ethyl acetate) R$_f$ 0.54; tlc (3:1 CHCl$_3$:methanol) R$_f$ 0.37.

Substitution of an equivalent of the appropriate carboxylic acid anhydride or acid chloride for acetic anhydride in this process yields compounds of the formula (III) wherein B=H, A$^1$=OH, R$^6$=CH$_3$CO, R$^7$=CH$_3$ and R$^1$=CH$_3$CH$_2$CO, CH$_3$(CH$_2$)$_2$CO, CH$_3$CH(CH$_3$)CO or CH$_3$CH$_2$CH(C$_2$H$_5$)CO.

By the same three stage process title product of Examples A1/C1 is converted to compound (IV, B=H, A$^1$=OH, R$^1$=R$^6$=CH$_3$CO, R$^7$=CH$_3$) and title product of Example C3 is converted to compound (V, A=OH, Y=oxygen, R$^1$=R$^8$=CH$_3$CO).

Omitting the first (protection) and third (deprotection) steps, the same acylation process is employed to convert title product of Example D1 to compound (IV, B=H, A$^1$=OSO$_2$(pCH$_3$C$_6$H$_4$), R$^1$=R$^6$=CH$_3$CO, R$^7$=CH$_3$), and title product of Example D3 is converted to compound (V, A=OSO$_2$(pCH$_3$C$_6$H$_4$), Y=NN(CH$_3$)$_2$, R$^1$=R$^8$=CH$_3$CO).

METHOD M

OXIDATION OF HYDROXYMETHYL TO FORMYL

EXAMPLE M1

Compound (III, B and A$^1$ together=oxygen, R$^1$=R$^6$=CH$_3$CO, R$^7$=CH$_3$) from Compound (III, B=H, A$^1$=OH, R$^1$=R$^6$=CH$_3$CO, R$^7$=CH$_3$)

Title product of Example L1 (2.7 g, 3.5 mmole) was dissolved in dimethylsulfoxide (0.99 ml, 14.0 mmole) and benzene (15 ml). 1-(3-Dimethylaminopropyl)-3-ethylcarbodimide (2.0 g, 10.5 mmole) was added, the mixture stirred 0.25 hour, then pyridinium trifluoroacetate (0.676 g, 3.5 mmole) was added. After an additional 0.5 hour, tlc indicated reaction complete. The reaction mixture was poured into 100 ml 1:1 H$_2$O:ethyl acetate, adjusted to from pH 6.2 to 4.0 with 1N HCl, and the organic layer separated, combined with 50 ml fresh H$_2$O and adjusted to pH 9.5 with 1N NaOH. The organic phase was again separated, dried and stripped to yield crude, unstable product as a foam, 2.6 g, tlc (ethyl acetate) R$_f$ 0.63. This product is stored at low temperature or used immediately in further process steps.

By the same method, other compounds of Example L1 are converted to compounds of the formula (III) wherein B and A$^1$ together=oxygen, R$^1$=CH$_3$CO, R$^7$=CH$_3$ and R$^6$=CH$_3$CH$_2$CO, CH$_3$(CH$_2$)$_2$CO, CH$_3$CH(CH$_3$)CO or CH$_3$CH$_2$CH(C$_2$H$_5$)CO; or compound (IV, B and A$^1$ together=oxygen, R$^1$=R$^6$=CH$_3$CO, R$^7$=CH$_3$).

METHOD N

REDUCTIVE AMINATION OF FORMYL

EXAMPLE N1

Compound (III, B=R$^6$=H, A$^1$=N(CH$_3$)$_2$, R$^1$=CH$_3$CO, R$^7$=CH$_3$) from Compound (III, B and A$^1$ together=oxygen, R$^1$=R$^6$=CH$_3$CO, R$^7$=CH$_3$)

Freshly prepared, crude title product of Example M1 (2.6 g, estimated 2.0 mmole) was dissolved in 45 ml methanol and dimethylamine hydrochloride (1.6 g, 20 mmole) added. The pH was adjusted to 5.5 with 6 drops glacial CH$_3$CO$_2$H and the mixture stirred 20 minutes. A solution of $NaBH_3CN$ (0.1 g, 1.32 mmole) in 5 ml methanol was added dropwise over 5 minutes and stirring continued two hours, at which time tlc indicated unreacted aldehyde. More $NaBH_3CN$ (0.05 g) was added, stirring continued 1.5 hours, the mixture poured into 200 ml 1:1 $H_2O$:ethyl acetate, and the pH adjusted to 2.0 with 1 N HCl. The aqueous phase was separated, adjusted to pH 4.0, 6.0 and 10.0 with 1N NaOH, extracting at each pH with 1×50 ml fresh ethyl acetate. The pH 10 extract was dried and stripped to a foam. To complete hydrolysis of the sugar acetates, the foam was taken up in methanol, stirred for 18 hours and stripped to a second foam (0.41 g). The second foam was distributed in 40 ml 1:1 $H_2O$:ethyl acetate at ph 6.4 (pH adjusted with 0.5N HCl). The aqueous phase was separated, adjusted to pH 6.8, 7.2 and 10.0 with 1N NaOH, extracting at each pH 1×20 ml ethyl acetate. The pH 7.2 and 10.0 extracts were combined, washed 1×40 ml $H_2O$ and adjusted to pH 6.4 with 0.5N HCl and the aqueous phase again adjusted to pH 6.8, 7.2 and 10.0, again extracting at each pH. The last pH 10.0 extract was dried and stripped to yield title product as a foam, 0.1 g; tlc (ethyl acetate) $R_f$ 0.06; tlc (3:1 acetone: methanol) $R_f$ 0.29.

By the same procedure, the other compounds of Example M1 are converted to compounds of the formula (III) wherein $B=R^6=H$, $A^1=N(CH_3)_2$, $R^1=CH_3CH_2CO$, $CH_3(CH_2)_2CO$, $CH_3CH(CH_3)CO$ or $CH_3CH_2CH(C_2H_5)CO$; or compound (IV, $B=R^6=H$, $A^1=N(CH_3)_2$, $R^1=CH_3CO$).

Substituting the appropriate amine.HCl for $(CH_3)_2NH.HCl$ in this process produces the following additional compounds of the formula (III) wherein $B=R^6=H$, $R^1=CH_3CO$, $R^7=CH_3$ and $A^1=N(C_2H_5)_2$, $N(iC_3H_7)_2$, $N(CH_3)(nC_4H_9)$, $N(CH_2)_7$, $N(CH_2)_4$ or $N(CH_2CH_2)_2O$.

METHOD O

REPLACEMENT OF SULFONYLOXY WITH AZIDO

EXAMPLE O1

Compound (III, $B=R^1=H$, $A^1=N_3$, $R^6=CH_3CO$, $R^7=CH_3$) from Compound (III, $B=R^1=H$, $A^1=OSO_2(pCH_3C_6H_4)$, $R^6=CH_3CO$, $R^7=CH_3$)

Title product of Example D5 (10.0 g, 11.4 mmole) and $LiN_3$ (1.7 g, 34.2 mmole) were combined in 100 ml acetone, refluxed 7 hours (by which time tlc indicated reaction complete), and then poured into 600 ml 1:1 $H_2O$:ethyl acetate. The organic layer was separated, dried, stripped to a foam (9.0 g) and chromatographed on 20 g silica gel with ether as eluant and monitoring by tlc. Clean product fractions were combined and evaporated to yield purified title product, 3.5 g; tlc (ether) $R_f$ 0.40; tlc (3:1 $CHCl_3$:methanol) $R_f$ 0.95.

By the same method, title products of Example D1 and D2 are converted, respectively, to compounds:
(IV, $B=R^1=H$, $A^1=N_3$, $R^6=CH_3CO$, $R^7=CH_3$);
(V, $A=N_3$, Y=oxygen, $R^1=H$, $R^8=CH_3CO$).

METHOD P

REDUCTION OF AZIDO TO AMINO

EXAMPLE P1

Compound (III, $B=R^1=H$, $A^1=NH_2$, $R^6=CH_3CO$, $R^7=CH_3$) from Compound (III, $B=R^1=H$, $A^1=N_3$, $R^6=CH_3CO$, $R^7=CH_3$)

Title product of Example O1 (1.8 g, 2.4 mmoles) and Lindlar catalyst (0.5 g) were combined in 50 ml of ethanol and hydrogenated at 20 psig for 18 hours. The reaction mixture was filtered and the filtrate stripped to a foam, which was taken up in 125 ml 3:2 $H_2O$:ethyl acetate and the pH adjusted to 2.0 with 1N HCl. The aqueous phase was separated, adjusted to pH 4.5 with 1N NaOH, extracted 1×50 ml fresh ethyl acetate, adjusted to pH 10.0 and extracted 1×75 ml fresh ethyl acetate. The pH 10.0 extract was dried and stripped to yield title product as a foam, 1.9 g; tlc (3:1 $CHCl_3$:methanol) $R_f$ 0.40; tlc (ether) $R_f$ 0.02.

By the same method, other compounds of Example O1 are converted to compounds:
(IV, $B=R^1=H$, $A^1=NH_2$, $R^6=CH_3CO$, $R^7=CH_3$);
(V, $A=NH_2$, Y=oxygen, $R^1=H$, $R^8=CH_3CO$).

METHOD Q

N-ACYLATION

EXAMPLE Q1

Compound (III, $B=R^1=H$, $A^1=NHSO_2(pCH_3C_6H_4)$, $R^6=CH_3CO$, $R^7=CH_3$) from Compound (III, $B=R^1=H$, $A^1=NH_2$, $R^6=CH_3CO$, $R^7=CH_3$)

Title product of Example P1 (1.4 g, 1.9 mmoles), p-toluenesulfonyl chloride (0.73 g, 3.8 mmole) and triethylamine (0.55 ml, 4.0 mmole) were combined in 30 ml $CH_2Cl_2$ and stirred one hour, by which time tlc indicated reaction was complete. The reaction was poured into 50 ml $H_2O$, stirred one hour and the pH then adjusted to 10.0 with 1N NaOH. The organic layer was separated, dried, stripped to a foam, and chromatographed on 30 g silica gel in a 20 mm diameter column, with 5 ml fractions of ether eluant collected. Fractions 80–140 were combined and stripped to yield title product, 0.46 g; tlc (ether) $R_f$ 0.14; $R_f$ (3:1 $CHCl_3$:methanol) 0.93.

The same procedure, substituting an equivalent amount of the appropriate acid chloride or acid anhydride for p-toluenesulfonyl chloride; yields additional compounds of the formula (III) wherein $B=R^1=H$, $R^6=CH_3CO$, $R^7=CH_3$ and $A^1=NHSO_2(nC_3H_7)$, $NHSO_2(iC_3H_7)$, $NHSO_2(pClC_6H_4)$, $NHSO_2CH_2C_6H_5$, $NHCOCH_3$, $NHCOCH_2CH(CH_3)_2$, $NHCO(CH_2)_3CH_3$, $NHCOC_6H_5$, $NHCO(mC_2H_5C_6H_4)$, $NHCO(3,5-Cl_2C_6H_3)$ or $NHCOCH_2(pCH_3OC_6H_4)$.

By the same method, other compounds of Example P1 are converted to the compounds:
(IV, $B=R^1=H$, $A^1=NHSO_2(pCH_3C_6H_4)$, $R^6=CH_3CO$, $R^7=CH_3$);
(V, $A=NHSO_2(pCH_3C_6H_4)$, Y=oxygen, $R^1=H$, $R^8=CH_3CO$).

PREPARATION 1

Fermentation of *Streptomyces Albus* ATCC 39012

Culture ATCC 39012 is considered to represent a new subspecies of *S. albus* and is named *Streptomyces albus* (Rossi Doria) Waksman and Henrici subsp. *indicus* Huang subsp. nov., and is on deposit at the American Type Culture Collection, Rockville, Md., U.S.A., under the above accession number. The permanency of the deposit of this culture at the American Type Culture Collection at Rockville, Md. and ready accessibility thereto by the public are afforded throughout the effective life of the present patent in the event the patent is granted. Access to the culture is available during pendency of the application under 37 CFR 1.14 and 35 USC 112. All restrictions on the availability to the public of the culture deposited will be irrevocably removed either upon granting of the present patent, or upon grant of copending patent application Ser. No. 374,223, filed May 3, 1982, whichever might occur earlier.

Shake flasks were prepared using the following medium:

| Ingredient | Amount (Grams/Liters) |
| --- | --- |
| Cerelose | 10 |
| Corn Starch | 20 |
| Yeast Extract (Difco) | 5 |
| NZ Amine A (Humko)* | 5 |
| Cobalt Chloride | 0.002 |
| Tap water to one liter, pH to 7.1–7.2 | |

*A purified enzymatic digest of casein.

The medium was distributed in 40 ml portions to 300 ml shake flasks, and it was then sterilized at 120° and 15 psi for 30 minutes. After cooling, the medium was inoculated with a vegetative cell suspension from the *Streptomyces albus* subsp. *indicus* slant culture ATCC 39012, grown on ATCC 172 medium in agar. The flasks were shaken at 28° on a rotary shaker having a displacement of 1½ to 2½" at 150 to 200 cycles per minute (CPM) for two to four days, then used to inoculate four liter fermentation vessels containing two liters of one of the following media:

| Ingredient | Amount (grams/liter) | Ingredient | Amount (grams/liter) |
| --- | --- | --- | --- |
| Cerelose | 10.0 | Cerelose | 1.0 |
| Corn Starch | 20.0 | NZ Amine Ytt* | 2.5 |
| Yeast BYF 300 | 5.0 | Corn Starch | 5.0 |
| NZ Amine Ytt(Humko)* | 5.0 | Corn Steep Liquor | 5 cc |
| Cobalt Chloride | 0.002 | Cobalt Chloride | 0.002 |
| Calcium Carbonate | 1.0 | Calcium Carbonate | 3.0 |
| pH 6.9–7.0 to 1 liter with water | | | |

*An enzymatic digest of casein.

One milliliter of antifoaming agent was added, and the vessels were sealed and sterilized at 120° and 15 psi for 45 minutes. The vessels were inoculated with one (2%) or two (4%) shake flasks, fermented for 12 to 30 hours at 30°, stirred at 1700 revolutions per minute (RPM) and air sparged through the broth at one volume per volume per minute. When fermentation was complete (based on antibiotic disc assay versus *B. subtilis* ATCC 6633), the fermentation was stopped, and the whole broth was filtered. The filtrate was extracted with methyl isobutyl ketone or ethyl acetate at pH 9.0. The organic phase was removed from the aqueous phase by aspiration, and then the organic phase was sparkled and concentrated in vacuo to a viscous oil.

PREPARATION 2

Isolation and Characterization of the Two Major Components from the *Streptomyces albus* subsp. *indicus* ATCC 39012 Fermentation Two 1,000 gallon fermentations of *Streptomyces albus* subsp. *indicus* ATCC 39012 were extracted with 300 gallons of methyl isobutyl ketone. The methyl isobutyl ketone was extracted twice with acidic water (pH 3.5) using 15 gallons of water each time. These extracts were combined and the pH was raised to 9.0 with 6N NaOH. The aqueous phase was then extracted with 7 gallons of chloroform. The chloroform was evaporated to a yellow oil (25 g). This oil was triturated with one liter of heptane and the solids thus generated were collected by filtration and washed with fresh heptane to give 2.6 g of a solid.

The above 2.6 g of solid was chromatographed on a 2.5 × 100 cm column packed with column grade silica gel 60 (Merck) in $CHCl_3$-MeOH-$NH_4OH$ (92:8:1). The same solvent system was used to elute the column. The flow rate was 10 ml/minute and one cut was taken every minute. The cuts were examined by thin layer chromatography and the cuts containing the two major antibiotic components were combined and evaporated in vacuo. This afforded 1.0 g of the antibiotic complex as a solid. This latter solid was rechromatographed on silica gel using the same conditions, to give 150 mg of antibiotic complex. The infrared spectrum of the antibiotic complex (KBr disc) showed significant absorption bands at 2.95, 3.45, 5.80, 6.20, 6.90, 7.25, 7.65, 8.30, 9.30, 9.95, 10.25 and 11.85 microns. The ultraviolet spectrum of the antibiotic complex (in methanol) showed absorption maxima at 238 millimicrons ($E_{1\%}$ 141) and 279 millimicrons ($E_{1\%}$ 80.5).

Analysis: Found: C, 59.00; H, 8.45; N, 1.48%.

PREPARATION 3

Separation of the Antibiotic Complex

The antibiotic complex was separated into its components utilizing a reverse phase $C_{18}$ silica gel column. The eluant used was methanol-water-2-aminoethanol (55:45:0.5). The flow rate was 5 ml/minute and one cut was taken every minute. The column was monitored with a 254 nm ultraviolet detector. The faster moving, major component eluted was the epoxide (CP-56,063), while the slower moving, minor component was the diene (CP-56,064). The following physicochemical data were determined for the individual components.

CP-56,063
   Molecular formula $C_{44}H_{75}O_{17}N$
   Molecular weight 889
   Melting point 210°–215° (dec.)
   Analysis: C, 58.90; H, 7.97; N, 1.69%
   Optical rotation $[alpha]_D = -57°$ (c=1, $CH_3OH$)
   Ultraviolet 238 nm; $E_{1\%}^{1\ cm} = 151$
   White amorphous solid.

The significant bands in the infrared spectrum over the region 4,000 to 200 $cm^{-1}$ are: (KBr disk) 3440, 2985, 2935, 1720, 1690, 1620, 1170 and 1080 $cm^{-1}$. Tlc (3:1 $CHCl_3$:methanol): $R_f$ 0.7.

CP-56,064
   Molecular formula $C_{44}H_{75}O_{16}N$
   Molecular weight 873
   Melting point 118°–130° (dec.)
   Ultraviolet 282 nm; $E_{1\%}^{1\ cm} = 186$
   Amorphous solid.

The solubilities of the two compounds are similar: soluble in chloroform, methanol, ethanol and ethyl acetate; insoluble in heptane and water.

PREPARATION 4

Intermediate Compound (Xa) by Selective Hydrolysis of CP-56,063 (VIII)

CP-56,063 of the preceding Preparation (0.1 g, 0.11 mmole) and p-toluenesulfonic acid monohydrate (0.042 g, 0.22 mmole) were combined in 5 ml of acetone and stirred for 90 minutes at room temperature, at which time tlc indicated that reaction was complete. The reaction mixture was diluted with water and ethyl acetate and the pH adjusted to 2.0 (dilute NaOH or HCl, as required). The aqueous layer was separated, adjusted to pH 5.0, extracted with ethyl acetate, adjusted to pH 10.0 and extracted with fresh ethyl acetate. The pH 10.0 extracted was dried and stripped of solvent to yield compound (Xa) as a foam, 0.07 g, tlc (3:1 CHCl$_3$.methanol): R$_f$0.25.

By the same method, CP-56,064 is converted to compound (IXa).

PREPARATION 5

Intermediate Compound (Xb, $R^7$=CH$_3$) by Dimethylacetalization of Compound (Xa)

To a solution of title product of the preceding Preparation (787 mg, 1 mmole) in 30 ml of methanol was added 15 ml of 1N methanolic HCl. The solution was stirred at 10° and 2 hours, then quenched with 5 ml of triethylamine and stirred 0.5 hour at ambient temperature. The solvent was evaporated and the residue redissolved in ethyl acetate. The ethyl acetate solution was washed with H$_2$O and saturated NaCl, dried and evaporated to yield compound (Xb, $R^7$=CH$_3$), as an amorphous foam, 700 mg, tlc (3:1 CHCl$_3$/MeOH): R$_f$0.43.

Substituting ethyl alcohol or ethylene glycol for methanol in this process yields the corresponding compounds (Xb, $R^7$=C$_2$H$_5$) or (Xb, both $R^7$ taken together—=—(CH$_2$)$_2$—).

Substituting compound (IXa) for (Xa) in this process yields intermediate compound (IXb, $R^7$=CH$_3$).

PREPARATION 6

Intermediate Compound (Xc, $R^7$=CH$_3$, $R^d$=CH$_3$CO) by Acetylation of Compound (Xc, $R^7$=CH$_3$)

Title product of the preceding Preparation (0.3 g, 0.36 mmole) and acetic anhydride (0.14 ml, 1.5 mmole) were combined in 20 ml of ethyl acetate and stirred for two hours, by which time tlc indicated reaction to be complete. The reaction mixture was diluted with H$_2$O and the pH slowly adjusted over 45 mintues to 9.5 with dilute NaOH. The organic layer was separated and evaporated to yield compound (Xc, $R^7$=CH$_3$, $R^c$=CH$_3$CO), 0.2 g, tlc (ethyl acetate) R$_f$0.42.

Substituting equivalent butyric anhydride for acetic anhydride in this process produces compound (Xc, $R^7$=CH$_3$, $R^c$=CH$_3$(CH$_2$)$_2$CO).

By the same process other compounds of the preceding Preparation are converted to:
(Xc, $R^7$=C$_2$H$_5$, $R^c$=CH$_3$CO)
(Xc, both $R^7$ taken together=—(CH$_2$)$_2$—, $R^c$=CH$_3$CO)
(IXc, $R^7$=CH$_3$, $R^c$=CH$_3$CO).

PREPARATION 7

Intermediate Compound (Xd, $R^7$=CH$_3$, $R^d$=CH$_3$CO) by (1H-1-Imidazolyl)carbonylation of Compound (Xc, $R^7$=CH$_3$, $R^d$=CH$_3$CO)

Title product of the preceding Preparation (0.2 g, 0.22 mmole), carbonyldiimidazole (0.07 g, 0.44 mmole) and triethylamine (0.03 ml, 0.22 mmole) were combined in 10 ml of acetonitrile and stirred for 64 hours at room temperature, by which time tlc indicated reaction complete. The reaction mixture was stripped to a foam. The foam was taken up in ethyl acetate, washed with water, dried and restripped to yield compound (Xc, $R^7$=CH$_3$, $R^d$=CH$_3$CO) as a foam, 0.2 g, tlc (ethyl acetate) R$_f$ 0.23.

By the same method, other compounds of the preceding Preparation are converted to:
(Xd, $R^7$=C$_2$H$_5$, $R^d$=CH$_3$CO)
(Xd, both $R^7$ together=—(CH$_2$)$_2$, $R^d$=CH$_3$CO)
(Xd, $R^7$=CH$_3$, $R^d$=CH$_3$(CH$_2$)$_2$CO)
(IXd, $R^7$=CH$_3$, $R^d$=CH$_3$CO).

PREPARATION 8

Intermediate Compound (Xe, $R^7$=CH$_3$, $R^d$=CH$_3$CO) by Trimethylsilation of Compound (Xd, $R^7$=CH$_3$, $R^d$=CH$_3$CO)

Title product of the preceding Preparation (0.2 g, 0.22 mmole), trimethylsilyl chloride (0.04 ml, 0.33 mmole), hexamethyldisilazane (0.015 g, 0.07 mmole) and imidazole (0.05 g, 0.66 mmole) were combined in 10 ml CH$_2$Cl$_2$ and stirred 1.5 hours at room temperature, by which time tlc indicated reaction to be complete. The reaction mixture was washed with H$_2$O, dried and stripped to yield compound (Xe, $R^7$=CH$_3$, $R^d$=CH$_3$CO), 0.18 g, tlc (ethyl acetate): R$_f$0.48.

By the same method, other compounds of the preceding Preparation are converted to:
(Xe, $R^7$=C$_2$H$_5$, $R^d$=CH$_3$CO)
(Xe, both $R^7$ together=—(CH$_2$)$_2$—, $R^d$=CH$_3$CO)
(Xe, $R^7$=CH$_3$, $R^d$=CH$_3$(CH$_2$)$_2$CO) (IXe, $R^7$=CH$_3$, $R^d$=CH$_3$CO).

PREPARATION 9

Intermediate Compound (Xf, $R^7$=CH$_3$, $R^d$=CH$_3$CO) by Selective Hydrolysis of Compound (Xe, $R^7$=CH$_3$, $R^d$=CH$_3$CO)

Title product of the preceding Preparation (0.18 g, 1.6 mmole) and K$_2$CO$_3$ (0.02 g, 1.6 mmole) were combined in 8 ml acetone and 4 ml H$_2$O and stirred two hours at room temperature, by which time tlc indicated reaction was complete. The reaction mixture was diluted with H$_2$O and extracted with ethyl acetate. The organic layer was dried and stripped to yield compound (Xe, $R^7$=CH$_3$, $R^d$=CH$_3$CO) as a foam, 0.16 g; tlc (ethyl acetate): R$_f$0.78; tlc (3:1 CHCl$_3$:acetone): R$_f$0.59.

By the same method, other compounds of the preceding Preparation are converted to:
(Xf, $R^7$=C$_2$H$_5$, $R^d$=CH$_3$CO)
(Xf, both $R^7$ together=—(CH$_2$)$_2$—, $R^d$=CH$_3$CO)
(Xf, $R^7$=CH$_3$, $R^d$=CH$_3$(CH$_2$)$_2$CO)
(IXf, $R^7$=CH$_3$, $R^d$=CH$_3$CO).

PREPARATION 10

Intermediate Compound (Xg, $R^7$=CH$_3$, $R^d$=CH$_3$CO) by Selective Oxidation of Compound (Xf, $R^7$=CH$_3$, $R^d$=CH$_3$CO)

Under nitrogen, in flame dried glassware, dimethylsulfoxide (0.25 ml, 3.6 mmole) was combined with 20 ml of CH$_2$Cl$_2$ and cooled to $-70°$. Trifluoroacetic anhydride (0.38 ml, 2.5 ml) was added portionwise, maintaining less than $-60°$. After 10 minutes, title product of the preceding Preparation (0.5 g, 0.51 mmole) in 5 ml CH$_2$Cl$_2$ was added dropwise maintaining less than $-50°$. The reaction mixture was stirred one hour while warming to $-20°$. Triethylamine (0.7 ml, 5 mmole) was added and the reaction warmed to room temperature. The reaction mixture was washed with H$_2$O, dried and stripped to yield compound (Xg, $R^7$=CH$_3$, $R^d$=CH$_3$CO) as a foam, tlc (4:1 CHCl$_3$:acetone): R$_f$ 0.72; tlc (ethyl acetate) 0.65. The entire batch was used in the next step.

By the same method, the other compounds of the preceding Preparation are converted to:

(Xg, $R^7=C_2H_5$, $R^d=CH_3CO$)
(Xg, both $R^7$ together=—$(CH_2)_2$—, $R^d=CH_3CO$)
(Xg, $R^7=CH_3$, $R^d=CH_3(CH_2)_2CO$)
(IXg, $R^7=CH_3$, $R^d=CH_3CO$).

PREPARATION 11

Intermediate Compound (Xh, $R^7=CH_3$, $R^d=CH_3CO$) by Selective Hydrolysis of Compound (Xg, $R^7=CH_3$, $R^d=CH_3CO$)

The entire bath of title product of the preceding Preparation was dissolved in 12 ml tetrahydrofuran and $H_2O$ added to the cloud point. The pH was adjusted to 2.0 with dilute HCl and the reaction mixture stirred 0.5 hour at room temperature. The pH was then adjusted to 9.5 with dilute NaOH and the mixture extracted with ethyl acetate. The ethyl acetate was dried ($Na_2SO_4$) and stripped to yield compound (Xh, $R^7=CH_3$, $R^d=CH_3CO$) as a foam, 0.3 g; tlc (4:1 $CHCl_3$:acetone): $R_f$ 0.48; tlc (3:1 $CHCl_3$:acetone: $R_f$ 0.72; tlc (ethyl acetate): $R_f$ 0.48.

By the same method the other compounds of the preceding Preparation are converted to:

(Xh, $R^7=C_2H_5$, $R^d=CH_3CO$)
(Xh, both $R^7$ together=—$(CH_2)_2$—, $R^d=CH_3CO$)
(Xh, $R^7=CH_3$, $R^d=CH_3(CH_2)_2CO$)
(IXh, $R^7=CH_3$, $R^d=CH_3CO$).

I claim:

1. A compound having the formula

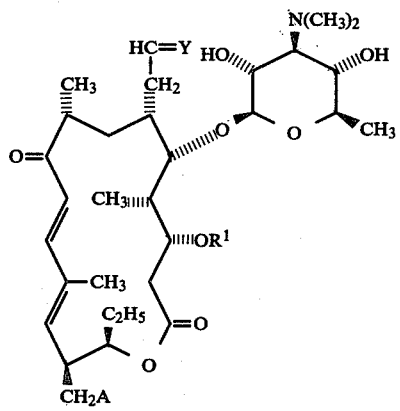

(I)

or

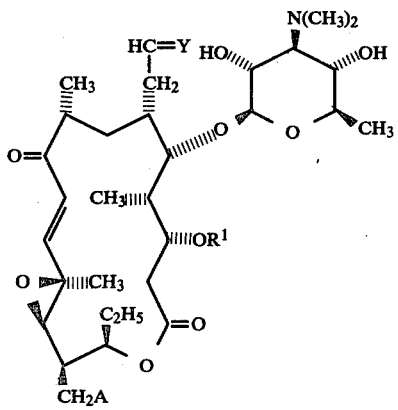

(II)

wherein
A is —XR, —OH, —$NR^2R^3$ or halo;
X is oxygen or NH;
Y is oxygen or $NNR^4R^5$;
R is ($C_2$-$C_6$)alkanoyl, ($C_8$-$C_{10}$)phenylalkanoyl, benzoyl, or one of ($C_1$-$C_6$)alkanesulfonyl or benzenesulfonyl, said phenylalkanoyl, benzoyl or benzenesulfonyl groups mono or disubstituted on aromatic ring with ($C_1$-$C_3$)-alkyl, ($C_1$-$C_3$)alkoxy or halo;
$R^1$ is hydrogen or ($C_2$-$C_6$)alkanoyl;
$R^2$ and $R^3$ are each independently ($C_1$-$C_6$)alkyl, or taken together are —$(CH_2)_2O(CH_2)_2$— or —$(CH_2)_n$—;
$R^4$ and $R^5$ are each independently H or ($C_1$-$C_6$)-alkyl, or taken together are —$(CH_2)_2O(CH_2)_2$— or —$(CH_2)_n$—; and
n is an integer from 4 to 7;
with the proviso that when the compound has the formula (I) and A is OH, $R^1$ is other than H; or a pharmaceutically acceptable acid addition salt thereof.

2. A compound of claim 1 having the formula (I).
3. A compound of claim 2 wherein A is —XR.
4. A compound of claim 3 wherein X is NH, Y is oxygen and $R^1$ is H.
5. A compound of claim 4 wherein R is benzenesulfonyl, or mono or disubstituted benzenesulfonyl.
6. The compound of claim 4 wherein R is p-toluenesulfonyl.
7. A compound of claim 3 wherein X and Y are oxygen.
8. A compound of claim 7 wherein $R^1$ is H.
9. The compound of claim 8 wherein R is acetyl.
10. A compound of claim 3 wherein X is oxygen and Y is $NNR^4R^5$.
11. A compound of claim 10 wherein $R^1$ is H.
12. A compound of claim 11 wherein R is benzenesulfonyl, or mono or disubstituted benzenesulfonyl, and $R^4$ and $R^5$ are methyl.
13. The compound of claim 12 wherein R is p-toluenesulfonyl.
14. A compound of claim 2 wherein A is $NR^2R^3$.
15. A compound of claim 14 wherein Y is oxygen.
16. A compound of claim 15 wherein $R^2$ and $R^3$ are methyl.
17. A compound of claim 16 wherein $R^1$ is ($C_2$-$C_6$)-alkanoyl.
18. The compound of claim 17 wherein $R_1$ is acetyl.
19. A compound of claim 2 wherein A is OH and $R^1$ is alkanoyl.
20. A compound of claim 19 wherein Y is oxygen.
21. The compound of claim 20 wherein $R^1$ is acetyl.
22. A compound of claim 2 wherein A is halo.
23. A compound of claim 22 wherein $R^1$ is H.
24. The compound of claim 23 wherein Y is oxygen and A is iodo.
25. The compound of claim 23 wherein Y is oxygen and A is chloro.
26. The compound of claim 23 wherein Y is $NNR^4R^5$, $R^4$ and $R^5$ are methyl and A is iodo.
27. A compound of claim 1 of the formula (II).
28. A compound of claim 27 wherein A is —$NR^2R^3$ and Y is oxygen.
29. A compound of claim 28 wherein $R^2$ and $R^3$ are taken together and are —$(CH_2)_2O(CH_2)_2$ or —$(CH_2)_n$—.
30. A compound of claim 29 wherein $R^2$ and $R^3$ are —$(CH_2)_7$—.

31. The compound of claim 30 wherein $R^1$ is hydrogen.

32. A compound of claim 30 wherein $R^1$ is $(C_2-C_6)$-alkanoyl.

33. The compound of claim 32 wherein $R^1$ is acetyl.

34. A compound having the formula

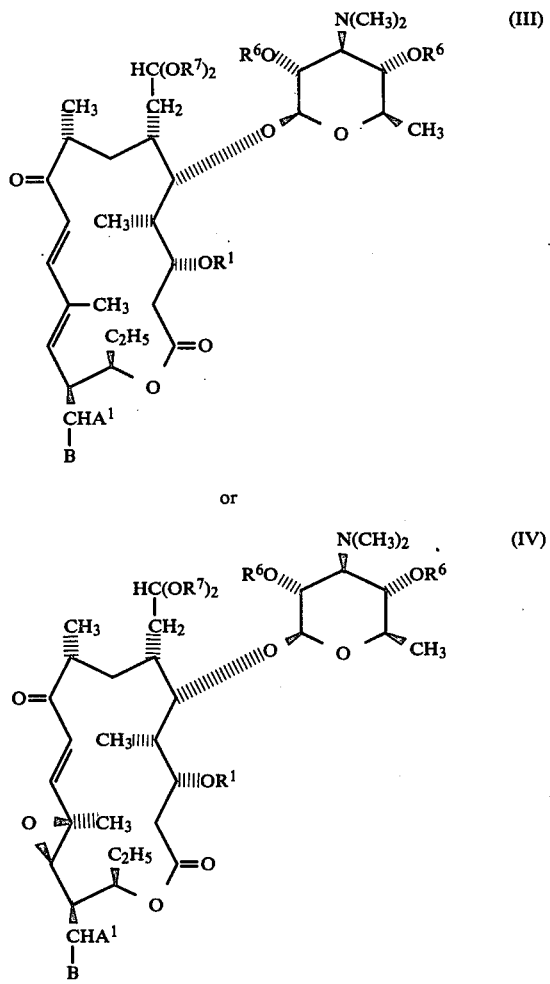

wherein

B is hydrogen and $A^1$ is —XR, —OH, —NH$_2$, —NR$^2$R$^3$, N$_3$ or halo; or

B and $A^1$ are taken together and are oxygen;

X is oxygen or NH;

R is $(C_2-C_6)$alkanoyl, $(C_8-C_{10})$phenylalkanoyl, benzoyl, $(C_1-C_6)$alkanesulfonyl or benzenesulfonyl or one of, said phenylalkanoyl, benzoyl or benzenesulfonyl groups mono or disubstituted on aromatic ring with $(C_1-C_3)$alkyl, $(C_1-C_3)$alkoxy or halo;

$R^1$ is hydrogen or $(C_2-C_6)$alkanoyl;

$R^2$ and $R^3$ are each independently $(C_1-C_6)$alkyl, or taken together are —(CH$_2$)$_2$O(CH$_2$)$_2$— or —(CH$_2$)$_n$—;

n is an integer from 4 to 7;

$R^6$ is H or $(C_2-C_6)$alkanoyl; and $R^7$ is $(C_1-C_4)$alkyl or the two $R^7$ groups are taken together and are $(C_2-C_3)$alkylene;

with the proviso that when the compound is of the formula (III) and $R^1$ and $R^6$ are both hydrogen, $A^1$ is other than —OH.

35. A compound of claim 34 having the formula (III).

36. A compound of claim 35 wherein $R^1$ is H, $R^6$ is acetyl and $R^7$ is methyl.

37. The compound of claim 36 wherein B is H, $A^1$ is —XR, X is oxygen and R is p-toluenesulfonyl.

38. The compound of claim 36 wherein B is H and $A^1$ is N$_3$.

39. The compound of claim 36 wherein B is H, A is —XR, X is oxygen and R is acetyl.

40. The compound of claim 36 wherein B is H and A is OH.

41. The compound of claim 36 wherein B is H and A is chloro.

42. The compound of claim 36 wherein B is H and A is NH$_2$.

43. A compound of claim 35 wherein $R^1$ and $R^6$ are H and $R^7$ is methyl.

44. The compound of claim 43 wherein B is H, $A^1$ is —XR, X is oxygen and R is acetyl.

45. A compound of claim 43 wherein B is H, $A^1$ is —XR, X is NH and R is p-toluenesulfonyl.

46. A compound of claim 35 wherein $R^1$ and $R^6$ are acetyl and $R^7$ is methyl.

47. The compound of claim 46 wherein B is H and $A^1$ is OH.

48. The compound of claim 46 wherein B and $A^1$ are taken together and are oxygen.

49. The compound of claim 46 wherein B is H, $A^1$ is NR$^2$R$^3$, and $R^2$ and $R^3$ are methyl.

50. A compound of claim 35 wherein $R^1$ is acetyl, $R^6$ is hydrogen and $R^7$ is methyl.

51. The compound of claim 50 wherein B is H, $A^1$ is NR$^2$R$^3$, and $R^2$ and $R^3$ are methyl.

52. The compound of claim 50 wherein B is H and $A^1$ is OH.

53. A compound of claim 34 having the formula (IV).

54. A compound of claim 53 wherein $R^1$ is H, $R^6$ is acetyl and $R^7$ is methyl.

55. The compound of claim 54 wherein B is H and $A^1$ is —OH.

56. A compound of claim 54 wherein B is H and $A^1$ is —XR, X is oxygen and R is benzenesulfonyl, or mono or disubstituted benzenesulfonyl.

57. The compound of claim 56 wherein R is p-toluenesulfonyl.

58. A compound of claim 54 wherein B is H and $A^1$ is —NR$^2$R$^3$.

59. A compound of claim 58 wherein $R^2$ and $R^3$ are taken together and are —(CH$_2$)$_2$O(CH$_2$)$_2$— or —(CH$_2$)$_n$—.

60. The compound of claim 59 wherein $R^2$ and $R^3$ are —(CH$_2$)$_7$—.

61. A compound having the formula

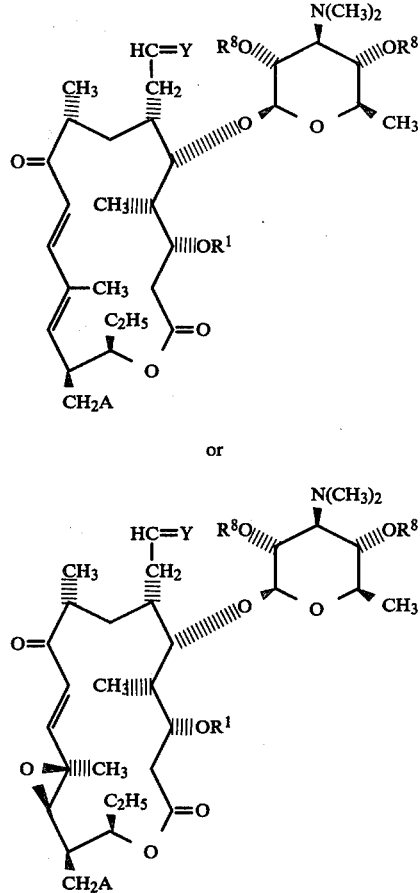

wherein
A is —XR, —OH, —NR²R³ or halo;
X is oxygen or NH;
Y is oxygen or NNR⁴R⁵;

R is $(C_2-C_6)$alkanoyl, $(C_8-C_{10})$phenylalkanoyl, benzoyl or one of, $(C_1-C_6)$alkanesulfonyl or benzenesulfonyl, said phenylalkanoyl, benzoyl or benzenesulfonyl groups mono or disubstituted or aromatic ring with $(C_1-C_3)$-alkyl, $(C_1-C_3)$alkoxy or halo;
$R^1$ is hydrogen or $(C_2-C_6)$alkanoyl;
$R^2$ and $R^3$ are each independently $(C_1-C_6)$alkyl, or taken together are —$(CH_2)_2O(CH_2)_2$— or —$(CH_2)_n$—;
$R^4$ and $R^5$ are each independently H or $(C_1-C_6)$-alkyl, or taken together are —$(CH_2)_2O(CH_2)_2$— or —$(CH_2)_n$—;
n is an integer from 4 to 7; and
$R^8$ is $(C_2-C_6)$alkanoyl.

62. A compound of claim 61 having the formula (V).
63. A compound of claim 62 wherein $R^8$ is acetyl.
64. A compound of claim 63 wherein $R^1$ is H and Y is oxygen.
65. A compound of claim 64 wherein A is —XR.
66. The compound of claim 65 wherein X is oxygen and R is p-toluenesulfonyl.
67. A compound of claim 63 wherein $R^1$ is H and Y is $NNR^4R^5$.
68. A compound of claim 67 wherein $R^4$ and $R^5$ are methyl.
69. A compound of claim 68 wherein A is —XR.
70. The compound of claim 69 wherein X is oxygen and R is p-toluenesulfonyl.
71. A compound of claim 68 wherein A is halo.
72. The compound of claim 71 wherein A is iodo.
73. A compound of claim 61 having the formula (VI).
74. A compound of claim 73 wherein $R^8$ is acetyl.
75. A compound of claim 74 wherein $R^1$ is H and Y is oxygen.
76. A compound of claim 75 wherein A is —$NR^2R^3$.
77. A compound of claim 76 wherein $R^2$ and $R^3$ are taken together and are —$(CH_2)_2O(CH_2)$— or —$(CH_2)_n$—.
78. The compound of claim 77 wherein $R^2$ and $R^3$ are —$(CH_2)_7$—.

* * * * *